US009144671B2

(12) United States Patent
Cantor et al.

(10) Patent No.: US 9,144,671 B2
(45) Date of Patent: Sep. 29, 2015

(54) TRANSDERMAL ADHESIVE PATCH ASSEMBLY WITH REMOVABLE MICRONEEDLE ARRAY AND METHOD OF USING SAME

(71) Applicant: 3M INNOVATIVE PROPERTIES COMPANY, St. Paul, MN (US)

(72) Inventors: Adam S. Cantor, River Falls, WI (US); Andrew J. Stockholm, Oak Park Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/352,327

(22) PCT Filed: Dec. 12, 2012

(86) PCT No.: PCT/US2012/069036
§ 371 (c)(1),
(2) Date: Apr. 17, 2014

(87) PCT Pub. No.: WO2013/096026
PCT Pub. Date: Jun. 27, 2013

(65) Prior Publication Data
US 2014/0243788 A1 Aug. 28, 2014

Related U.S. Application Data

(60) Provisional application No. 61/578,551, filed on Dec. 21, 2011.

(51) Int. Cl.
*A61M 31/00* (2006.01)
*A61M 37/00* (2006.01)
*A61K 9/70* (2006.01)

(52) U.S. Cl.
CPC ............ *A61M 37/0015* (2013.01); *A61K 9/703* (2013.01); *A61K 9/7084* (2013.01); *A61M 2037/0023* (2013.01); *A61M 2037/0061* (2013.01)

(58) Field of Classification Search
CPC . A61K 9/7084; A61K 9/703; A61M 37/0015; A61M 2037/0061; A61M 2037/0023
USPC ......... 604/46, 48, 49, 289, 173, 501, 22, 307, 604/304, 306, 180; 602/48, 49, 50
See application file for complete search history.

(56) References Cited

U.S. PATENT DOCUMENTS

| 4,472,480 A | 9/1984 | Olson |
| 4,584,355 A | 4/1986 | Blizzard |

(Continued)

FOREIGN PATENT DOCUMENTS

| JP | 2012-024240 | 2/2012 |
| WO | WO 2007-002523 | 1/2007 |

(Continued)

OTHER PUBLICATIONS

International Search Report for PCT International Application No. PCT/US2012/069036 mailed on Mar. 26, 2013, 4 pages.

*Primary Examiner* — Aarti B Berdichevsky
*Assistant Examiner* — Hamza Darb
(74) *Attorney, Agent, or Firm* — Nicole J. Einerson

(57) ABSTRACT

A transdermal adhesive patch assembly and method of using same. The assembly can include a backing, and an adhesive and a matrix coupled to the backing. The matrix can include an active ingredient. The assembly can further include a microneedle array in at least partially overlapping relationship with the matrix; and a carrier that couples the microneedle array to the matrix opposite the backing, wherein the carrier and the microneedle array form a skin treatment assembly that, along with the matrix, can be located on a flap. The method can include adhering at least a portion of the adhesive to skin to form an anchor; applying pressure adjacent the microneedle array to treat an area of the skin; moving the flap away from the skin; removing the skin treatment assembly to expose the matrix; and replacing the flap to position the matrix over the treated area of the skin.

20 Claims, 7 Drawing Sheets

(56) References Cited

U.S. PATENT DOCUMENTS

| | | | |
|---|---|---|---|
| 4,585,836 A | 4/1986 | Homan | |
| 4,591,622 A | 5/1986 | Blizzard | |
| 4,627,429 A | 12/1986 | Tsuk | |
| 4,655,767 A | 4/1987 | Woodard | |
| 4,693,776 A | 9/1987 | Krampe | |
| 4,751,087 A | 6/1988 | Wick | |
| 4,815,457 A | 3/1989 | Mazars | |
| 4,834,979 A | 5/1989 | Gale | |
| 5,223,261 A | 6/1993 | Nelson | |
| 5,380,760 A | 1/1995 | Wendel | |
| 5,531,855 A | 7/1996 | Heinecke et al. | |
| 5,656,286 A | 8/1997 | Miranda | |
| 5,688,523 A | 11/1997 | Garbe | |
| 5,738,647 A * | 4/1998 | Bernhard et al. | 604/20 |
| 5,783,269 A | 7/1998 | Heilmann | |
| 6,004,578 A | 12/1999 | Lee | |
| 6,024,976 A | 2/2000 | Miranda | |
| 6,091,975 A | 7/2000 | Daddona | |
| 6,126,929 A | 10/2000 | Mougin | |
| 6,129,929 A | 10/2000 | Wick | |
| 6,149,935 A | 11/2000 | Chiang | |
| 6,312,612 B1 | 11/2001 | Sherman | |
| 6,365,178 B1 | 4/2002 | Venkateshwaran | |
| 6,379,324 B1 | 4/2002 | Gartstein | |
| 6,745,071 B1 | 6/2004 | Anderson et al. | |
| 7,141,034 B2 | 11/2006 | Eppstein | |
| 2003/0054025 A1 | 3/2003 | Cantor | |
| 2004/0049150 A1 | 3/2004 | Dalton | |
| 2004/0202708 A1 | 10/2004 | Roehrig | |
| 2005/0261631 A1 | 11/2005 | Clarke | |
| 2008/0195035 A1 * | 8/2008 | Frederickson et al. | 604/22 |
| 2008/0262284 A1 | 10/2008 | Marcenyac | |
| 2008/0274146 A1 | 11/2008 | Bartholomaus | |
| 2008/0274166 A1 * | 11/2008 | Sacks et al. | 424/449 |
| 2009/0216169 A1 | 8/2009 | Hansen | |
| 2011/0040166 A1 | 2/2011 | Okada | |
| 2011/0077608 A1 * | 3/2011 | Macedo, Jr. | 604/385.01 |
| 2011/0237925 A1 | 9/2011 | Yue | |
| 2011/0251561 A1 | 10/2011 | Inou | |

FOREIGN PATENT DOCUMENTS

| | | |
|---|---|---|
| WO | WO 2008-091878 | 7/2008 |
| WO | WO 2009-047774 | 4/2009 |
| WO | WO 2010-140760 | 12/2010 |
| WO | WO 2011-066493 | 6/2011 |
| WO | WO 2012-074576 | 6/2012 |
| WO | WO 2012-122162 | 9/2012 |
| WO | WO 2013-090353 | 6/2013 |

* cited by examiner

TRANSDERMAL ADHESIVE PATCH ASSEMBLY WITH REMOVABLE MICRONEEDLE ARRAY AND METHOD OF USING SAME

CROSS REFERENCE TO RELATED APPLICATIONS

This is a national stage filing under 35 U.S.C. §371 of PCT Application No. PCT/US2012/069036, filed Dec. 12, 2012, which claims priority to U.S. Provisional Application No. 61/578,551, filed Dec. 21, 2011, the disclosure of which is incorporated herein by reference in its entirety.

FIELD

The present disclosure generally relates to transdermal adhesive patch assemblies that can be used to treat an area of skin and apply an active ingredient to the treated area of skin, as well as methods of using such transdermal adhesive patch assemblies.

BACKGROUND

Transdermal and topical drug delivery can be used for therapeutic treatment, but the number of molecules that can be effectively delivered using these routes can be limited by the barrier properties of skin.

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

In some cases, these treatments are provided by a single integrated device that performs two separate functions: the device treats the skin and also delivers an active ingredient to the treated skin. An example would be a hollow microneedle array with an attached drug reservoir. The microneedles pierce the skin and remain attached while the drug flows from the reservoir into the skin. Although devices of this type may be conceptually easy for a patient to administer, they can be complex and/or limited in the amount of drug they can effectively deliver.

SUMMARY

The present disclosure relates to transdermal adhesive patch assemblies that can be used to treat a selected site (e.g., on skin), and to apply an active ingredient to the treated site. One feature and advantage of assemblies of the present disclosure is that they can ensure that the matrix comprising the active ingredient can be accurately aligned with the treated area on the skin, as the typical skin treatments are microscopic in nature and thus the treated skin will generally not have a different appearance from untreated skin. In addition, the transdermal adhesive patch assemblies of the present disclosure generally include a skin treatment device (i.e., a microneedle array) that can be used in a first step to perform the function of treating the skin to increase permeability and/or create pores. The skin treatment device can then be removed and, in a second step, the matrix can be placed on the site of the treated skin to perform the second function of delivering the active ingredient to the treated skin. Although this includes an additional user step, the separation of skin treatment from drug delivery can afford simplicity in device design, as well as providing flexibility in the design to better match the specific needs of these two different functions.

One aspect of the present disclosure provides a transdermal adhesive patch assembly. The assembly can include a backing having a first major surface and a second major surface, and a skin-contact adhesive coupled to the second major surface of the backing. The assembly can further include a matrix comprising an active ingredient, the matrix coupled to the second major surface of the backing. The assembly can further include a microneedle array located in at least partially overlapping relationship with the matrix; and a carrier positioned to couple the microneedle array to the matrix opposite the backing, wherein the carrier and the microneedle array form a skin treatment assembly that can be decoupled from the matrix, when desired, to expose the matrix. A portion of the backing and at least a portion of the skin-contact adhesive can extend beyond the skin treatment assembly in at least one direction to form an anchor. The matrix and the skin treatment assembly can be located on a flap that is movable with respect to the anchor between a first position in which the flap is not folded back relative the anchor and a second position in which the flap is folded back relative to the anchor.

Another aspect of the present disclosure provides a method of treating skin and applying an active ingredient transdermally. The method can include providing a transdermal adhesive patch assembly. The assembly can include a backing having a first major surface and a second major surface; a skin-contact adhesive coupled to the second major surface of the backing; a matrix comprising an active ingredient, the matrix coupled to the second major surface of the backing; a microneedle array located in at least partially overlapping relationship with the matrix; and a carrier positioned to couple the microneedle array to the matrix opposite the backing, the carrier and the microneedle array forming a skin treatment assembly. The method can further include adhering at least a portion of the skin-contact adhesive to the skin to form an anchor, wherein the matrix and the skin treatment assembly are located on a flap that is movable with respect to the anchor. The method can further include applying pressure adjacent the microneedle array to treat an area of the skin; moving the flap away from the skin while the anchor remains adhered to the skin; removing the skin treatment assembly to expose the matrix; and replacing the flap to position the matrix in least partially overlapping relationship with the treated area of the skin.

Other features and aspects of the present disclosure will become apparent by consideration of the detailed description and accompanying drawings.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof is used broadly and encompasses both direct and indirect couplings. It is to be understood that other embodiments may be utilized, and structural or logical changes may be made without departing from the scope of the present disclosure. Furthermore, terms such as "front," "rear," "first," "second," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a transdermal adhesive patch assembly that includes a means for treating skin (i.e., for creating small holes or perforations or micropores in a biological membrane) to prepare the skin for delivery of an active ingredient, and means for positioning a matrix comprising the active ingredient over the treated area of the skin (or biological membrane), such that the matrix is positioned to at least partially overlap the treated area. Particularly, assemblies of the present disclosure include a removable skin treatment assembly comprising a carrier and a microneedle array that can be positioned over the matrix in a skin treatment configuration, and which can be removed following treatment of the skin to expose the matrix for delivery. The present disclosure accomplishes placing the matrix over the treated area using facile means that do no require specific predetermined fold or hinge lines, but rather allow a user to adhere a patch to skin, treat the skin with the microneedle array, peel back a flap that includes the skin treatment assembly covering the matrix, remove the skin treatment assembly to expose the matrix, and replace the flap onto the skin, such that the matrix is positioned at least partially over the treated area of the skin for delivery, e.g., of an active ingredient.

Figure 1:
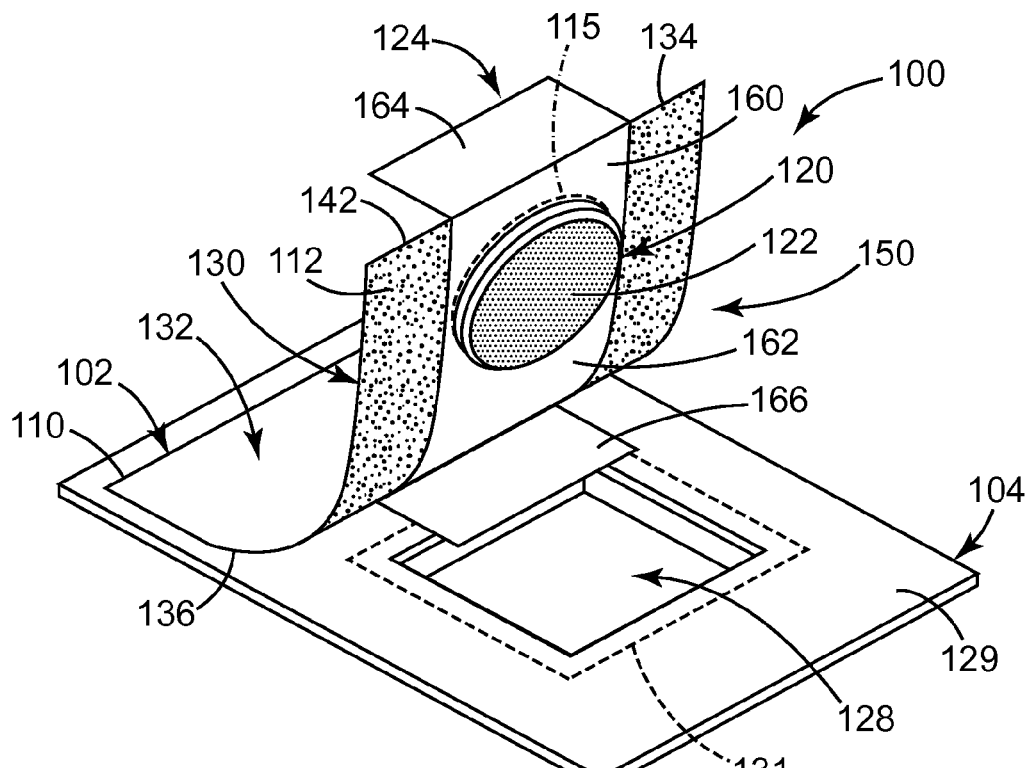
FIG. 1 is a perspective view of a transdermal adhesive patch assembly according to one embodiment of the present disclosure.
Figure 2:
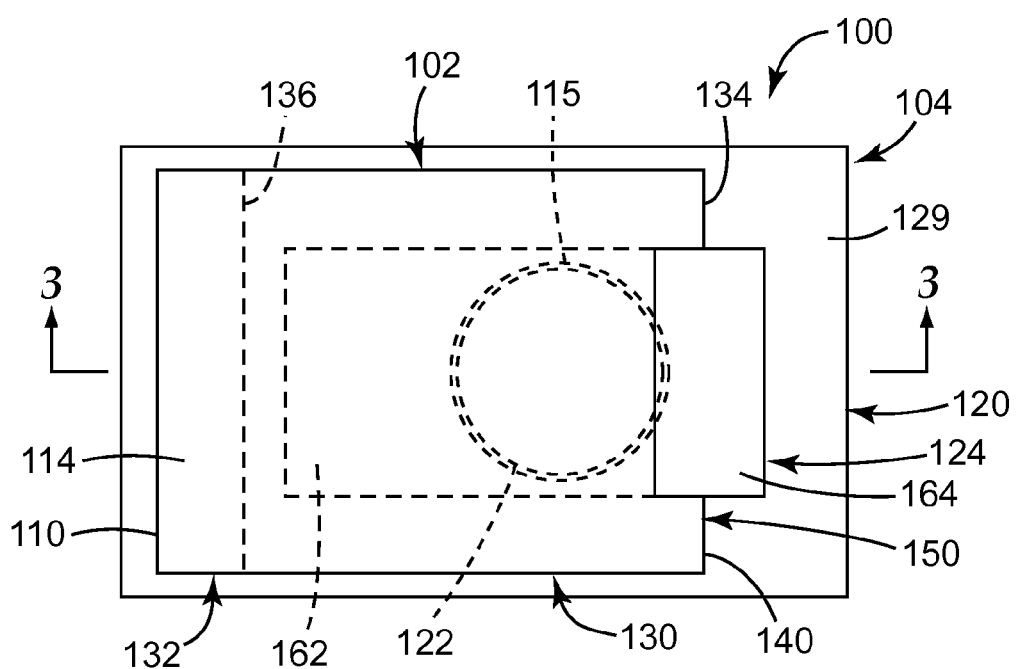
FIG. 2 is a top plan view of the transdermal adhesive patch assembly of FIG. 1.
Figure 3:
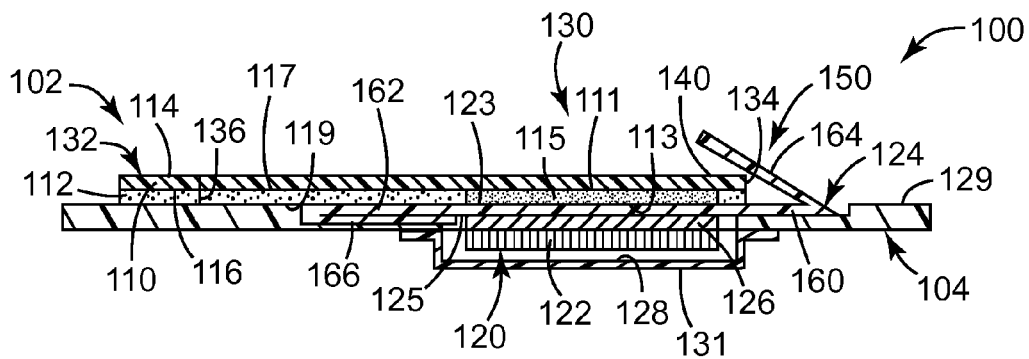
FIG. 3 is a schematic side cross-sectional view of the transdermal adhesive patch assembly of FIGS. 1 and 2, taken along line 3-3 of FIG. 2.

FIGS. 1-3 illustrate a transdermal adhesive patch assembly 100 according to one embodiment of the present disclosure, and FIGS. 4A-4D illustrate a method of treating skin and applying an active ingredient transdermally, using the transdermal adhesive patch assembly 100 of FIGS. 1-3.

The transdermal adhesive patch assembly 100 can include an adhesive patch 102 and a release liner (or layer) 104. In some embodiments, the adhesive patch 102 can include a transdermal drug delivery patch comprising a drug that can be administered via skin, particularly, mammalian skin, and particularly transdermally.

The term "transdermally" is generally used to refer to any type of delivery of an active ingredient that crosses any portion of skin. That is, transdermally can generally include systemic delivery (i.e., where the active ingredient is transported across, or substantially through, the dermis such that the active ingredient is delivery into the bloodstream and systemically), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The patch 102 can include a backing 110, and an adhesive 112, e.g., a skin-contact adhesive (such adhesive can also be referred to as an "adhesive layer" or a "skin-contact layer"). The backing 110 can include a first major surface 114 and a second major surface 116 opposite the first major surface 114, and the skin-contact adhesive 112 can be coupled (i.e., directly, or indirectly via one or more optional additional layers, as described below) to the second major surface 116.

The patch 102 (or the transdermal adhesive patch assembly 100) can further include a matrix 115 comprising an active ingredient (or "active," or "active agent," or "medicament"—e.g., a drug). The matrix 115 can also be coupled to the second major surface 116 of the backing 110, either directly, or indirectly via one or more optional additional layers. For example, in some embodiments, the matrix 115 can be coupled to the backing 110 via an adhesive, which can include the skin-contact adhesive 112, or can be a separate and/or different adhesive. In some embodiments, the matrix 115 can be coupled to the backing 110 via a barrier layer which is adhered to the skin-contact adhesive 112. The barrier layer can prevent or minimize interaction between the matrix 115 and one or both of the skin-contact adhesive 112 and the backing 110. The matrix 115 can be positioned next to, or within an area of, the skin-contact adhesive 112, as shown in FIGS. 1-3, such that the matrix 115 and the skin-contact adhesive 112 do not substantially overlap, or the matrix 115 can at least partially overlap the skin-contact adhesive 112. Alternatively, in some embodiments, a portion of the skin-contact adhesive 112 can comprise an active ingredient and thus serve as the matrix 115.

The term "matrix" is generally used to refer to a material in which something is enclosed or embedded. The matrix 115 can be configured to achieve a desired transport/delivery rate of the active ingredient. In some embodiments, the matrix 115 can be, or include, a polymeric matrix, for example, a hydrogel that is capable of swelling and retaining an aqueous liquid.

The transdermal adhesive patch assembly 100 can further include a skin treatment assembly (or "microneedle array assembly" 120, at least a portion of which can be removably coupled to the patch 102. In some embodiments, the patch 102 can be described as including the skin treatment assembly 120. The skin treatment assembly 120 can be coupled over the matrix 115 to protect and cover the matrix 115 during a skin treatment step, and the skin treatment assembly 120 can be removable from the matrix 115 and/or other components of the transdermal adhesive patch assembly 100, for example, after the skin treatment assembly 120 has been used to treat the skin and when delivery of the active ingredient is desired.

The skin treatment assembly 120 can include a microneedle array 122 and a carrier 124 positioned to couple the microneedle array 122 to the matrix 115 opposite the backing 110, and optionally to at least a portion of the skin-contact adhesive 112 (i.e., opposite the backing 110).

Figure 4A:
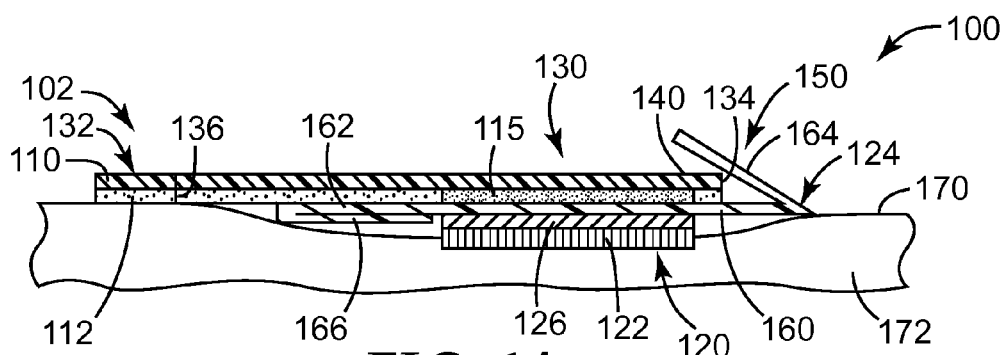
FIGS. 4A-4D a method of treating skin and applying an active ingredient transdermally according to one embodiment of the present disclosure, using the transdermal adhesive patch assembly of FIGS. 1-3 shown in schematic side cross-sectional views.
Figure 4B:
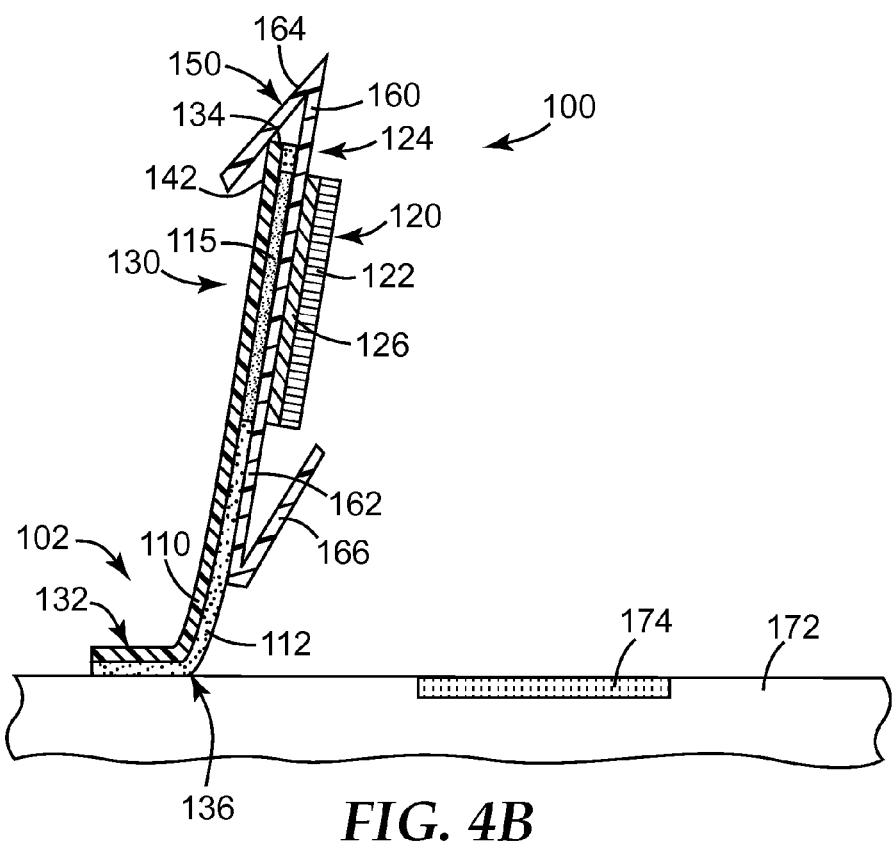
Figure 4C:
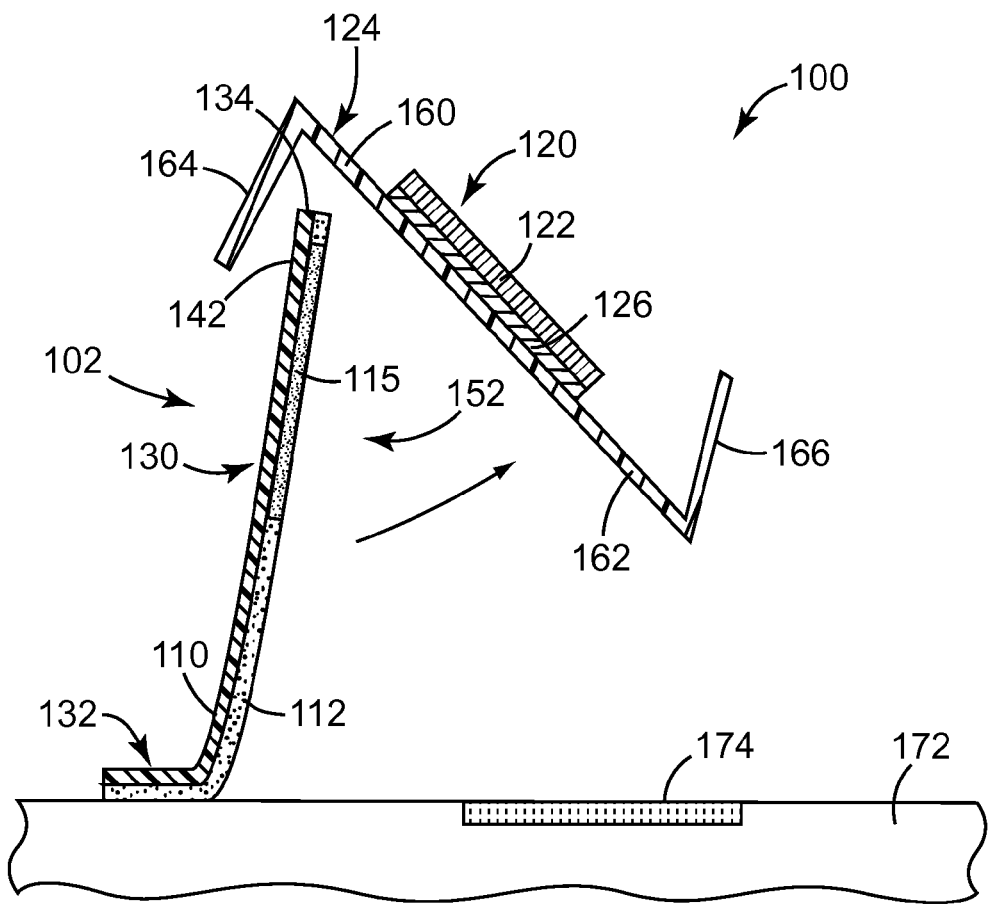

As shown, the transdermal adhesive patch assembly 100 can include a first portion, or flap, 130 that is movable with respect to a second portion, or anchor, 132 between a first position 140 (see FIGS. 2, 3, 4A and 4D) in which the flap 130 is not folded back relative to the anchor 132, and a second position 142 (see FIGS. 1, 4B and 4C). The flap 130 can include a free end 134 that can be generally opposite the anchor 132, and a fixed end that can generally be adjacent the anchor 132.

The anchor 132 can generally include a portion of the backing 110 and at least a portion of the skin-contact adhesive 112. The flap 130 can include the matrix 115 and the skin treatment assembly 120, such that the flap 130 can be positioned in the first position 140 during skin treatment and during delivery of the active ingredient, and can be peeled back into the second position 142, for example, after skin treatment to remove the skin treatment assembly 120 and expose the matrix 115 for delivery of the active ingredient.

The flap 130 and the anchor 132 need not be separated by a discrete fold or hinge about which the flap 130 is pivoted. Rather, the flap 130 can be pivoted about any point or line (which need not be a straight line), as chosen by the user, depending on which portion of the skin-contact adhesive 112 is first adhered to the skin to form the anchor 130.

As will be described in greater detail below with respect to FIGS. 4A-4D, the transdermal adhesive patch assembly 100 (and the skin treatment assembly 120) can include a first, or skin treatment, configuration 150 (see FIGS. 1-3 and 4A-4B) where the skin treatment assembly 120 is coupled to and covering the matrix 115, and a second, or delivery configuration 152 (see FIGS. 4C-4D) wherein the skin treatment assembly 120 is removed, or decoupled, from the matrix 115, and the matrix 115 is exposed. Particularly, when the transdermal adhesive patch assembly 100 is in the skin treatment configuration 150, the microneedle array 122 can be located in at least partially overlapping relationship with the matrix 115, such that after skin has been treated with the microneedle array 122, the microneedle array 122 can be removed, and the matrix 115 can be positioned on the skin in at least partially overlapping (and preferably, fully overlapping) relationship with the treated area of the skin.

In the first position 140, the flap 130 can be described as being generally co-planar with the anchor 132, such that in the first position 140, the flap 130 is generally in the plane of the anchor 132, and in the second position 142, the flap 130 is generally out of the plane of the anchor 132. When the flap 130 and the anchor 132 are substantially co-planar, the flap 130 and the anchor 132 generally reside in the same plane, i.e., the flap 130 and the anchor 132 are oriented at a "zero" angle with respect to one another, while allowing for slight undulations or raised areas that may protrude out of the plane. In the second position 142, the flap 130 can be described as being peeled back or folded back, e.g., relative to a plane of the anchor 132, where the flap 130 and the anchor 132 are oriented at a non-zero angle with respect to one another, such that the flap and the anchor no longer reside in the same plane or are no longer co-planar.

As shown in FIG. 3, the matrix 115 can include a first major surface 111 and a second major surface 113, and the skin-contact adhesive 112 can include a first major surface 117 and a second major surface 119, and the carrier 124 can be coupled to the second major surface 113 of the matrix 115, and optionally, to the second major surface 119 of the skin-contact adhesive 112. The carrier 124 can include a first major surface 123 that can be coupled to the matrix 115 (e.g., to the second major surface 113 of the matrix 115) and optionally, to the skin-contact adhesive 112 (e.g., to the second major surface 119 of the skin-contact adhesive 112). The carrier 124, and particularly, the first major surface 123 of the carrier 124, can be configured to release, or can be configured to present release characteristics to, at least one of the matrix 115 and the skin-contact adhesive 112. The carrier 124 can further include a second major surface 125 to which the microneedle array 122 can be coupled. In some embodiments, the carrier 124 can be formed of a material that presents release characteristics to the matrix 115 and/or the skin-contact adhesive 112. In some embodiments, this material can be in the form of a molded (e.g., injection molded) material (e.g., of a polyolefin), and in such embodiments, the carrier 124 and the microneedle array 122 can be integrally formed. The molded material itself can present release characteristics, or the first major surface 123 of the carrier 124 can be modified or coated, e.g., with a release agent, as described in greater detail below. In some embodiments, the carrier 124 can be formed of at least one of paper, a plastic film, or any other suitable release layer or liner material described below.

In some embodiments, the matrix 115 can include an adhesive or be adhesive relative to skin. In embodiments in which the matrix 115 includes a skin adhesive, the matrix 115 can include the same adhesive or a different adhesive as that forming the skin-contact adhesive 112. For example, in some embodiments, the matrix 115 can be weakly adhesive to skin, relative to the skin-contact adhesive 112. In some embodiments, the skin-contact adhesive 112 may not surround the entire area or zone of the matrix 115, so in such embodiments, an adhesive matrix that can remain adhered to skin for the desired duration of treatment may be beneficial. In other embodiments, in which the skin-contact adhesive 112 surrounds the matrix 115, the matrix itself can be weakly adhesive or non-adhesive.

In embodiments in which the matrix 115 is not adhesive, the carrier 124 can be coupled to the matrix 115 by an adhesive located between the matrix 115 and the carrier 124. In some embodiments, such an adhesive can have greater affinity for the carrier 124, so that the adhesive can also form a portion of the skin treatment assembly 120 and be removed from the matrix 115 when the skin treatment assembly 120 is removed, to leave the matrix exposed. Alternatively, in some embodiments in which the matrix 115 is not adhesive, the carrier 124 can be dimensioned to cover the matrix 115 as well as a portion of the skin-contact adhesive 112, such that the skin treatment assembly 120 is located over the matrix 115 and is adhered by the skin-contact adhesive 112. In such embodiments, the carrier 124 can be configured as a release layer for (i.e., and present release characteristics to) the skin-contact adhesive 112.

In addition, the release liner 104 can be configured to release, or can be configured to present release characteristics to, the skin-contact adhesive 112, so that the patch 102 (along with the skin treatment assembly 120) can be coupled to the release liner 104 during storage and shipment, and can be easily removed from the release liner 104 during application of the patch 102.

A surface that is "configured to release" or "configured to present release characteristics relative to" an adhesive (such as the skin-contact adhesive 112 or the matrix 115, if the matrix 115 is adhesive) is a surface that generally has a surface energy that is less than that of the adhesive, such that the adhesive does not adhere or does not adhere well to the surface. Generally, "low surface energy" surfaces (i.e., low, relative to a particular adhesive) or surfaces that present "release characteristics" do not allow the adhesive to "wet out" the surface, so that strong adhesion does not occur between the adhesive and the surface with the low surface energy. Such low energy surfaces can be provided by a variety of materials (e.g., polyolefins), or such low energy surfaces can be provided by a surface modification, e.g., by coating the surface with a release agent. Examples of various materials and release agents that can be employed in the carrier 124 and/or the release liner 104 are described in greater detail below.

The phrase "does not adhere well," or variations thereof, can generally refer to an adhesive having a 90 degree peel strength, at least initially, of less than about 50 g, in some embodiments, less than about 30 g, and in some embodiments, less than about 20 g, when a 1-inch-(2.54 cm)-wide strip of the adhesive (e.g., the skin-contact adhesive 112 coupled to the backing 110) is peeled from another surface (e.g., a first major surface 129 of the release liner 104 and/or the first major surface 123 of the carrier 124).

The phrase "adheres well," or variations thereof, can generally refer to an adhesive having a 90 degree peel strength, at least initially, of at least about 500 g, in some embodiments, at least about 800 g, and in some embodiments, at least about 1000 g (1 kg), when a 1-inch-(2.54 cm)-wide strip of the adhesive (e.g., the skin-contact adhesive 112 coupled to the backing 110) is peeled from another surface (e.g., the skin to which the skin-contact adhesive 112 is configured to be adhered).

As shown in FIG. 3, in some embodiments, the microneedle array 122 can be coupled to the carrier 124 (i.e., the second major surface 125 of the carrier 124) with an adhesive 126. The adhesive 126 is shown as a coupling means between the carrier 124 and the microneedle array 122 by way of example only; however, it should be understood that the microneedle array 122 can be coupled to the carrier 124 by a variety of coupling means, including, but not limited to, press-fit or friction-fit engagement, snap-fit engagement, magnets, hook-and-loop fasteners, adhesives, cohesives, clamps, heat sealing, stitches, staples, screws, nails, rivets, brads, crimps, welding (e.g., sonic (e.g., ultrasonic) welding), any thermal bonding technique (e.g., heat and/or pressure applied to one or both of the components to be coupled), other suitable coupling means, or combinations thereof. Alternatively, in some embodiments, the carrier 124 can include the microneedle array 122, and the microneedle array 122 can be integrally formed with the carrier 124.

In embodiments employing an adhesive-type of coupling, the coefficient of adhesion between the microneedle array 122 and the carrier 124 can be greater than the coefficient of adhesion between the carrier 124 and the matrix 115 and/or greater than the coefficient of adhesion between the carrier 124 and the skin-contact adhesive 112, if applicable, such that in some embodiments, the skin treatment assembly 120 can be removed from the matrix 115 and/or the skin-contact adhesive 112 as a whole unit.

In addition, in general, the coefficient of adhesion (1) between the carrier 124 and the matrix 115 and/or between the carrier 124 and the skin-contact adhesive 112 is generally less than the coefficient of adhesion (2) between the backing 110 and the skin-contact adhesive 112 (even if the skin-contact adhesive 112 is indirectly coupled to the backing 110; is also generally less than the coefficient of adhesion (3) between the backing 110 and the matrix 115, if applicable (even if the matrix 115 is indirectly coupled to the backing 110); and is generally less than the coefficient of adhesion (4) between the carrier 124 and the microneedle array 122. Such relative coefficients of adhesion can ensure that the patch 102 does not delaminate during application, and that the skin treatment assembly 120 can be easily and cleanly removed as a whole after treatment of the skin.

As a result, the transdermal adhesive patch assemblies of the present disclosure generally rely on relative coefficients of adhesion and release characteristics in order to sequentially treat skin and apply an active ingredient to the treated site, rather than requiring that specific portions or sheets of the assembly be cleanly torn off at various stages. In addition, because of these adhesive relationships, the skin treatment assembly 120 and the matrix 115 can be located on the same flap 130 that is movable relative to the anchor 132, rather than requiring a plurality of flaps that are sequentially positioned and/or removed from the assembly.

In some embodiments, as shown in FIGS. 1 and 3, the release liner 104 can include a recess, depression or cavity 128 that can be dimensioned to receive at least a portion of the skin treatment assembly 120. For example, in some embodiments, the recess 128 can be dimensioned to receive the microneedle array 122, and in some embodiments, the recess 128 can be further dimensioned to receive at least a portion of the carrier 124. In some embodiments, as shown in FIGS. 1 and 3, the recess 128 can be formed in a housing 131 (i.e., a "skin treatment assembly housing") that can be provided by, coupled to, or integrally formed with, the release liner 104. Generally, the recess 128 can be dimensioned to receive and house at least a portion of the skin treatment assembly 120, such that the surfaces of the housing 131 do not contact the skin treatment assembly 120 (and particularly, do not contact the microneedle array 122), e.g., to preserve the effectiveness of the microneedle array 122. In some embodiments, the recess 128 can be shaped and dimensioned to predominantly receive the microneedle array 122, and may also at least partially house the carrier 124, for example, if the microneedle array 122 and the carrier 124 generally take up the same area, as shown in FIGS. 1-3. Alternatively, in some embodiments, the recess 128 can include a portion that is dimensioned to receive the microneedle array 122 and another portion that is dimensioned to receive at least a portion of the carrier 124. In some embodiments, one housing 131 can be shaped and dimensioned to house both the microneedle array 122 and the carrier 124, and in some embodiments, separate recesses 128 can be employed, depending at least in part on the arrangement and configuration of the skin treatment assembly 120. In some embodiments, at least a portion of at least one recess 128 can be provided by the patch 102 instead of, or in addition to, being provided by the release liner 104. Similar to that described above with respect to the release liner 104, such a recess can be formed in the patch 102, or can be formed in a housing provided by, coupled to, or integrally formed with, the patch 102.

With continued reference to the embodiment of FIGS. 1-4D, in some embodiments, the carrier 124 can include at least one extension that can facilitate (i) grasping the carrier 124, (ii) moving the flap 130 between the first position 140 and the second position 142, and/or (iii) removing the skin treatment assembly 120 (e.g., decoupling the skin treatment assembly 120 from the matrix 115 or other components of the transdermal adhesive patch assembly 100).

By way of example only, the transdermal adhesive patch assembly 100 shown in FIGS. 1-4D includes a first extension 160 that can extend beyond an edge of the backing 110 (and the matrix 115 and the microneedle array 122), e.g., toward or past the free end 134 of the flap 130, so that it can be accessible even when the flap 130 is in the first position 140. The first extension 160 generally extends in a direction opposite from the anchor 132, and can be positioned and/or configured to be grasped to peel the flap 130 back to move the flap 130 from the first position 140 to the second position 142 (e.g., toward the anchor 132 (see FIGS. 4B-4C)).

By way of further example, the transdermal adhesive patch assembly 100 of FIGS. 1-4D includes a second extension 162 that can be positioned and/or configured to be grasped to facilitate decoupling the skin treatment assembly 120 from the matrix 115 (or from a position in which the skin treatment assembly 120 covers the matrix 115). In some embodiments, as shown in FIGS. 1-4B, the second extension 162 can extend beyond the microneedle array 122 in a direction that is different (e.g., opposite) than that of the first extension 160. That is, the second extension 162 can extend toward the fixed end 136 of the flap 130 For example, as shown in FIGS. 1-4A, when the flap 130 is in the first position 140, the second extension 162 can extend beyond the matrix 115 and the microneedle array 122 toward the anchor 132 and toward the fixed end 136 of the flap 130.

In some embodiments, one or both of the first extension 160 and the second extension 162 can include a tab 164, 166 that can be folded back relative to the extension 160, 162, respectively, to facilitate grasping. For example, as shown in FIGS. 1-4C, in some embodiments, the first extension 160 can include a tab 164 that can be folded back toward the backing 110 (e.g., in a direction toward the fixed end 136 of the flap 130), and in some embodiments, is folded back over an edge of the backing 110 to facilitate grasping, e.g., when the flap 130 is in the first position 140. As further shown in FIGS. 1-4C, in some embodiments, the second extension 162 can include a tab 166 that can be folded back toward the microneedle array 122 (e.g., in a direction toward the free end 136 of the flap 130) to facilitate grasping to decouple the skin treatment assembly (i.e., the carrier 124) from the matrix 115 and/or the skin-contact adhesive 112 (or other components of the transdermal adhesive patch assembly 100), for example, when the flap 130 is in the second position 142. As shown in FIG. 3, when the flap 130 is in the first position 140, the tab 166 can be folded or collapsed upon itself.

Other variations of the extensions 160, 162 and tabs 164, 166 are possible, and some are described in greater detail below with respect to FIGS. 6-11.

With reference to FIGS. 4A-4D, a method for using the transdermal adhesive patch assembly 100 to treat skin and deliver an active ingredient (e.g., transdermally) will now be described. First, the release liner 104 (if used) can be removed from the rest of the transdermal adhesive patch assembly 100 (e.g., from the patch 102 and the skin treatment assembly 120).

As shown in FIG. 4A, the transdermal adhesive patch assembly 100 can then be pressed onto a desired surface to be treated, e.g., a surface 170 of skin 172. The transdermal adhesive patch assembly 100 is in the first, or skin treatment configuration 150, and the flap 130 is folded down in the first position 140. Pressure (e.g., finger pressure) can be applied adjacent the skin-contact adhesive 112 in the anchor 132 to anchor a portion of the transdermal adhesive patch assembly 100 to the skin 172. Simultaneously, or sequentially, pressure (e.g., finger pressure) can be applied to the backing 110 adjacent the microneedle array 122 to press the microneedle array 122 into the stratum corneum of the skin 172 to treat the skin 172 and make holes or micropores in the skin 172 to facilitate delivery of an active ingredient.

As shown in FIG. 4B, after the skin 172 has been treated with the microneedle array 122, the flap 130 (e.g., the free end 134 of the flap 130) can be moved (e.g., folded back, peeled back, or the like) from the first position 140 to the second position 142 to expose the microneedle array 122 and a treated area 174 of the skin 172, while the anchor 132 remains adhered to the skin 172 via the skin-contact adhesive 112. The flap 130 can be moved by grasping the tab 164 of the first extension 160 of the carrier 124 and pulling the flap 130 back, e.g., toward the anchor 132.

As shown in FIG. 4C, the skin treatment assembly 120 can be removed, or decoupled, from the matrix 115 and/or the skin-contact adhesive 112 (or other components of the transdermal adhesive patch assembly 100) to change the transdermal adhesive patch assembly 100 from the skin treatment configuration 150 to the delivery configuration 152, and to expose the matrix 115, which can include an active ingredient. The skin treatment assembly 120 can be removed by grasping the tab 166 of the second extension 162 and pulling (e.g., peeling) the carrier 124 toward the free end 134 of the flap 130.

Figure 4D:
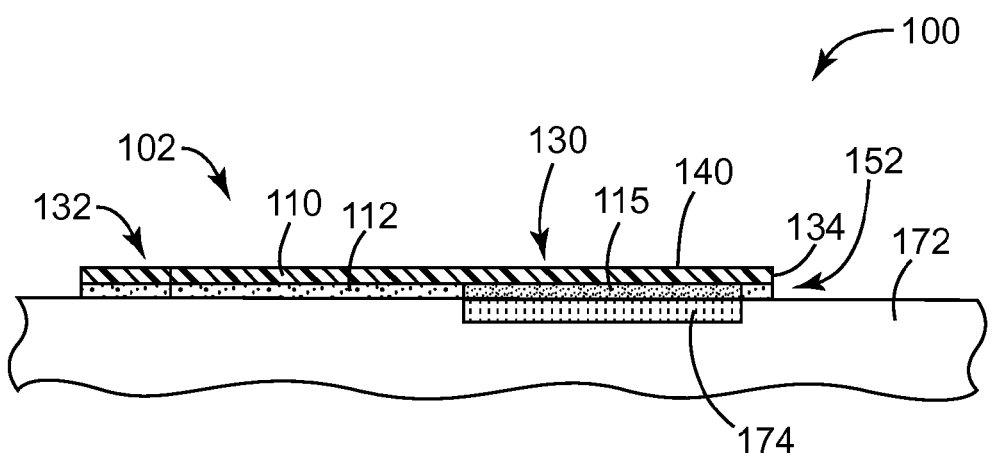

As shown in FIG. 4D, after the skin treatment assembly 120 has been removed and the matrix 115 has been exposed, the flap 130 can be folded back down, i.e., moved from the second position 142 to the first position 140. Because the anchor 132 was never moved from when it was first adhered to the skin 172, and because of the arrangement and overlap of the various layers of the transdermal adhesive patch assembly 100, when the flap 130 is replaced over the sin 172, the matrix 115 can at least partially overlap the treated area 174 of the skin 172. In some embodiments, the matrix 115 can exactly and fully overlap the treated area 174 of the skin 172 to maximize the effectiveness of the transdermal delivery of the active ingredient from the matrix 115. In some embodiments, the surface area of the matrix 115 can be slightly larger (up to about 1% or up to about 5% or up to about 10% larger) than the treated area 174 of the skin 172, and in particular can be dimensioned so that the matrix 115 extends a small amount beyond the treated area 174 of the skin 172 on all sides. Such a configuration can help ensure that the treated area 174 of the skin 172 is completely covered by the matrix 115, even in the event of a slight misalignment.

In some embodiments, the patch 102 can further include one or more optional additional layers between the backing 110 and the skin-contact adhesive 112, such that the skin-contact adhesive 112 is still coupled, but not directly coupled, to the second major surface 116 of the backing 110. Such additional layer(s) may include, for example, tie layers that enhance the coupling between the backing 110 and the skin-contact adhesive 112; a permeation rate-controlling membrane; a protective barrier layer that prevents interaction between an active ingredient and the backing 110; or combinations thereof.

The backing 110 of the patch 102 can be formed of a variety of materials, including flexible films. Examples of flexible films that can be employed as a backing 110 for the patch 102 can include those made from polymer films such as polypropylene; polyethylene, particularly low density polyethylene, linear low density polyethylene, metallocene polyethylenes, and high density polyethylene; polyvinyl chloride; polyester (e.g., polyethylene terephthalate); polyvinylidene chloride; ethylene-vinyl acetate (EVA) copolymer; polyurethane; cellulose acetate; and ethyl cellulose. Coextruded multilayer polymeric films can also be suitable, such as those described in U.S. Pat. No. 5,783,269 (Heilmann et al.), the disclosure of which is incorporated herein by reference. Backings 110 that are layered such as polyethylene terephthalate-aluminum-polyethylene composites and polyethylene terephthalate-EVA composites can also be suitable. Foam tape backings, such as closed cell polyolefin films used in 3M™ 1777 Foam Tape and 3M™ 1779 Foam Tape (available from 3M Co., St. Paul, Minn.) can also be suitable. Polyethylenes, polyethylene blends, polyethylene composites, and polyurethanes can be preferred polymer films. Polyethylenes and polyurethanes can be optimal polymer films. In one embodiment, the backing 110 can be a translucent or transparent film. Additives may also be added to films used as a backing 110, such as tackifiers, plasticizers, colorants, and anti-oxidants.

The patches 102 of the present disclosure, and particularly the backings 110 (e.g., the first major surface 114 of the backing 110) may also include a release agent coating or a low adhesion coating, as described above. One example of a suitable low adhesion coating can be coated as a solution of polyvinyl N-octadecyl carbamate and a blend of silicone resins, as described in U.S. Pat. No. 5,531,855 (Heinecke et al.), the disclosure of which is incorporated herein by reference.

In some embodiments, the thickness of the backing 110 (or other optional additional layers in the patch 102) can be at least about 10 µm, in some embodiments, at least about 20 µm, and in some embodiments, at least about 40 µm. In some embodiments, the thickness of the backing 110 can be less than about 2 mm (0.07874 inch), in some embodiments, less than about 1 mm (0.03937 inch), and in some embodiments, less than about 150 microns (5906 microinches).

The skin-contact adhesive 112 is generally a pressure-sensitive adhesive, and particularly is a pressure-sensitive adhesive that is capable of securely but releasably adhering or bonding to skin (e.g., mammalian skin). The skin-contact adhesive 112 is also generally safe and non-toxic. Skin-contact adhesive layers will generally be selected according to the desired end use of the patch 102. In some embodiments, the patch 102 can include more than one skin-contact adhesive 112. Where the patch 102 comprises more than one skin-contact adhesive layer 112, each skin-contact adhesive layer 112 may be selected independently of each other with regard to material and thickness used. Examples of suitable adhesives include acrylates, silicones, polyisobutylenes, synthetic rubber, natural rubber, and copolymers and mixtures thereof. Acrylates and silicones can be preferred skin-contact adhesives 112. In general, the skin-contact adhesive 112 should cause little or no irritation or sensitization of the skin during the intended wear period.

In some embodiments, the skin-contact adhesive 112 can be an acrylate (or methacrylate) copolymer. Acrylates will typically have an inherent viscosity greater than about 0.2 dL/g and will comprise one or more polymerized primary monomers and optionally one or more polar comonomers. Primary monomers suitable for use include alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. In some embodiments, the alkyl acrylates can include isooctyl acrylate, 2-ethylhexyl acrylate, n-butyl acrylate, and cyclohexyl acrylate. Polar monomers suitable for use can include those having hydroxyl, amide, or carboxylic, sulfonic, or phosphonic acid functionality. Representative examples include acrylamide, methacrylamide, N-vinyl-2-pyrrolidone, 2-hydroxyethylacrylate, 2-hydroxyethylmethacrylate, hydroxypropylacrylate, acrylic acid, methacrylic acid, pyrrolidonyl ethyl acrylate, and alkoxyethyl acrylates, such as 2-carboxyethylacrylate. In some embodiments, the amount by weight of polar monomer will not exceed about 40% of the total weight of all monomers in order to avoid excessive firmness of the final PSA product. Typically, polar monomer can be incorporated to the extent of about 1% to about 20% by weight. In some embodiments, the polar monomer can be acrylamide.

In some embodiments, the acrylate copolymer can comprise the reaction product of primary and polar monomers and additional optional monomers which, when present, are included in the polymerization reaction in quantities that will not render the adhesive composition non-tacky. The optional additional monomers may be added, for example, to improve performance, reduce cost, or for other purposes. Examples of such optional monomers include vinyl esters, such as vinyl acetate, vinyl chloride, vinylidene chloride, styrene, and macromonomers copolymerizable with the other monomers.

Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference.

Silicone or polysiloxane pressure-sensitive adhesives include pressure-sensitive adhesives which are based on two major components: a polymer, or gum, and a tackifying resin. The polysiloxane adhesive can be prepared by cross-linking the gum, typically a high molecular weight polydiorganosiloxane, with the resin, to produce a three-dimensional silicate structure, via a condensation reaction in an appropriate organic solvent. The ratio of resin to polymer can be adjusted in order to modify the physical properties of polysiloxane adhesives. Use of capped (or amine-compatible) polysiloxanes can, in some embodiments, be preferred so as to increase drug stability and reduce degradation. Further details and examples of silicone pressure-sensitive adhesives which can be useful are described in the U.S. Pat. No. 4,591,622 (Blizzard et al.); U.S. Pat. No. 4,584,355 (Blizzard et al.); U.S. Pat. No. 4,585,836 (Homan et al.); and U.S. Pat. No. 4,655,767 (Woodard et al.). Suitable silicone pressure-sensitive adhesives are commercially available and include the silicone adhesives sold under the trademarks BIO-PSA® by Dow Corning Corporation, Medical Products, Midland, Mich.

Further description of suitable adhesives may be found in U.S. Pat. No. 5,656,286 (Miranda et al.), U.S. Pat. No. 5,223,261 (Nelson et al.), and U.S. Pat. No. 5,380,760 (Wendel et al.), the disclosures of which are incorporated herein by reference. In some embodiments, the thickness of the skin-contact adhesive 112 can be at least about 10 μm, in some embodiments, at least about 20 μm, and in some embodiments, at least about 40 μm. In some embodiments, the thickness of the skin-contact adhesive 112 can be less than about 2 mm (0.07874 inch), in some embodiments, less than about 1 mm (0.03937 inch), and in some embodiments, less than about 150 microns (5906 microinches).

As mentioned above, in some embodiments, active ingredients or agents (e.g., drugs) can be employed in the matrix 115, but can also optionally be included in the skin-contact adhesive 112 or in one or more additional layers in the patch 102. Examples of pharmaceutically active agents (also referred to as "drugs") that can be included in the reservoir are capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204, 219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl]methanesulfonamide, and acyclovir); local anesthetics (e.g., benzocaine, propofol, tetracaine, prilocalne); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatripan, zolmitriptan); antiarrhythmic agents (e.g., flecamide); antiemetics (e.g., metaclopromide, ondansetron, granisetron hydrochloride); anticancer agents (e.g., methotrexate); neurologic agents such as anxiolytic drugs; hemostatics; antiobesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, drugs that are of a large molecular weight may be delivered transdermally. Increasing molecular weight of a drug typically causes a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include flu vaccine, Lyme disease vaccine, rabies vaccine, measles vaccine, mumps vaccine, chicken pox vaccine, small pox vaccine, hepatitis vaccine, pertussis vaccine, rubella vaccine, diphtheria vaccine, encephalitis vaccine, yellow fever vaccine, recombinant protein vaccine, DNA vaccines, polio vaccine, therapeutic cancer vaccine, herpes vaccine, pneumococcal vaccine, meningitis vaccine, whooping cough vaccine, tetanus vaccine, typhoid fever vaccine, cholera vaccine, tuberculosis vaccine, and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Publication No. 2004/0049150 (Dalton et al.), the disclosure of which is hereby incorporated by reference.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

In some embodiments, the matrix 115 can be, or include, a drug reservoir. The size of such a drug reservoir can be suitable to deliver a selected amount of drug through the skin. Generally, the reservoir can have a surface area of at least about 0.5 cm$^2$, in some embodiments, at least about 1.0 cm$^2$, and in some embodiments, at least about 5 cm$^2$. Generally, the reservoir can have a surface area of less than about 100 cm$^2$, and in some embodiments, less than about 40 cm$^2$. The reservoir can have the same surface area as the patch 102, but it will typically be smaller in surface area than the patch 102 (e.g., will fit within the flap 130). In some embodiments, the reservoir can be centrally placed within the patch 102, such that it can be surrounded on all sides by a rim of skin-contact adhesive 112 that can help to secure the drug reservoir in place on a skin surface. The thickness of the drug reservoir can be at least about 10 μm, in some embodiments, at least about 20 μm, and in some embodiments, at least about 40 μm. In some embodiments, the drug reservoir thickness can be less than about 2 mm (0.07874 inch), in some embodiments, less than about 1 mm (0.03937 inch), and in some embodiments, less than about 150 microns (5906 microinches).

In some embodiments, the drug reservoir can be provided in the form of a transdermal patch adhered to the skin-contact adhesive 112 of the patch 102. Any transdermal patch suitable for the continuous transdermal delivery of a therapeutically effective amount of an appropriate medicament may be used. Suitable transdermal patches include gelled or liquid reservoirs, such as in U.S. Pat. No. 4,834,979 (Gale), so-called "reservoir" patches; patches containing matrix reservoirs attached to the skin by an adjacent adhesive layer, such as in U.S. Pat. No. 6,004,578 (Lee et al.), so-called "matrix" patches; and patches containing PSA reservoirs, such as in U.S. Pat. No. 6,365,178 (Venkateshwaran et al.), U.S. Pat. No. 6,024,976 (Miranda et al.), U.S. Pat. No. 4,751,087 (Wick) and U.S. Pat. No. 6,149,935 (Chiang et al.), so-called "drug-in-adhesive" patches, the disclosures of which are hereby incorporated by reference. In some embodiments, the reservoir can have an impermeable backing that substantially or fully inhibits migration of drug and/or excipients from the reservoir into the skin-contact adhesive 112 of the patch 102. Selection of an appropriate impermeable backing will depend upon the composition of the reservoir and one skilled in the art may readily determine a suitable backing by testing dressings for drug and/or excipient migration.

Typical impermeable barriers include films containing one or more polyethylene terephthalate layers and/or an aluminum barrier layer. In some embodiments, the impermeable backing can function to limit oxygen and/or water vapor permeation. Examples of impermeable backings can include films having plasma-deposited amorphous glass layers, such as described in WO 2011/066493 (Kluge et al. to 3M), and films having translucent inorganic barrier layers, such as described in US 2004/202708 (Roehrig et al. to 3M).

As mentioned above, the matrix 115 can be an adhesive layer and can include any of the adhesives described above. Alternatively, the matrix 115 can be non-adhesive or weakly adhesive and rely upon an adjacent portion (or surrounding rim) of the skin-contact adhesive 112 to secure the patch 102 in place and keep the drug reservoir in contact with the skin surface.

In another embodiment, the drug reservoir can be provided in the form of solid particles embedded on or adhered to the surface, or embedded within the skin-contact adhesive 112 of the patch 102. In particular, these particles may be hydrophilic, so that contact with aqueous fluid exposed at the surface of the treated skin will cause them to dissolve or disintegrate, thus releasing drug into the skin.

In some embodiments, a drug reservoir can be provided within the skin-contact adhesive 112 of the patch 102. The drug can be mixed with the skin-contact adhesive 112 prior to forming the patch 102 or it may be applied to the skin-contact adhesive 112 of the patch 102 in a separate process step. Examples of suitable methods for applying drug to an adhesive layer may be found in U.S. Patent Application Publication No. 2003/054025 (Cantor et al.) and U.S. Pat. No. 5,688,523 (Garbe et al.), the disclosures of which are hereby incorporated by reference.

Release liners, which can be used as at least a portion of the carrier 124 and the release liner 104, are available from a variety of manufacturers in a wide variety of proprietary formulations. Those skilled in the art will normally test those liners in simulated use conditions against an adhesive of choice to arrive at a product with the desired release characteristics. The materials used to supply the liners for the transdermal adhesive patch assemblies 100 of the present disclosure can be substantially more rigid than the backing 110, but this need not be the case. Liners which can be suitable for use in transdermal adhesive patch assemblies 100 of the present disclosure can be made of kraft papers, polyethylene, polypropylene, polyester or composites of any of these materials. The liners material can be coated with release agents or low adhesion coatings, such as fluorochemicals or silicones. For example, U.S. Pat. No. 4,472,480 (Olson), the disclosure of which is hereby incorporated by reference, describes low surface energy perfluorochemical liners. The liners can be papers, polyolefin films, or polyester films coated with silicone release materials. Examples of commercially available silicone coated release papers are POLYSLIK® silicone release papers available from Loparex (Willowbrook, Ill.).

In some embodiments, the length of time that the matrix 115 remains on the skin and in a delivering relationship may be an extended time, for example, from about 12 hours to about 14 days. In some embodiments, the duration of time that the matrix 115 remains in a delivering relationship can be about 1 day (i.e., daily dosing), about 3 to 4 days (i.e., bi-weekly dosing), or about 7 days (i.e., weekly dosing).

In some embodiments, the duration of time that the matrix 115 remains in a delivering relationship may be relatively short, for example from about 1 minute to about 1 hour, in some embodiments, from about 5 minutes to about 40 minutes, and in some embodiments, from about 5 minutes to about 20 minutes.

Microneedle arrays useful as skin treatment devices may comprise any of a variety of configurations, such as those described in the following patents and patent applications, the disclosures of which are each incorporated herein by reference. One embodiment for the microneedle arrays comprises the structures disclosed U.S. Patent Application Publication No. 2005/0261631 (Clarke et al.), which describes microneedles having a truncated tapered shape and a controlled aspect ratio. Still another embodiment for the microneedle arrays comprises the structures disclosed in U.S. Pat. No. 6,091,975 (Daddona et al.), which describes blade-like microprotrusions for piercing the skin. Still another embodiment for the microneedle arrays comprises the structures disclosed in U.S. Pat. No. 6,312,612 (Sherman et al.), which describes tapered structures having a hollow central channel. Still another embodiment for the microneedle arrays comprises the structures disclosed in U.S. Pat. No. 6,379,324 (Gartstein et al.), which describes hollow microneedles having at least one longitudinal blade at the top surface of the tip of the microneedle. Still, various embodiments of microneedles that can be employed in the microneedle arrays of the present disclosure are described in PCT Publication No. WO2012/074576 (Duan et al.), which describes liquid crystalline polymer (LCP) microneedles; and U.S. Provisional Patent Application No. 61/449,993, which describes a variety of different types and compositions of microneedles that can be employed in the microneedle arrays of the present disclosure.

Transdermal adhesive patch assemblies 100 of the present disclosure may be packaged individually in a foil-lined pouch for storage. Other materials, such as multi-laminate polymer films with low moisture and/or oxygen permeability may also be suitable for pouching dressings of the present disclosure. In order to improve storage stability, an optional desiccant and/or oxygen absorber may also be included within a hermetically sealed pouch containing the transdermal adhesive patch assembly 100. Transdermal adhesive patch assemblies 100 of the present disclosure may alternatively be provided in a rolled or stacked form suitable for use with a dispensing apparatus.

Additional exemplary embodiments of transdermal adhesive patch assemblies of the present disclosure will now be described with respect to FIGS. 5-12. FIGS. 5-12 illustrate various transdermal adhesive patch assemblies of the present disclosure, wherein like numerals represent like elements. The transdermal adhesive patch assemblies of FIGS. 5-12 share many of the same elements, features, and functions as those described above with respect to FIGS. 1-4D. Reference is made to the description above accompanying FIGS. 1-4D for a more complete description of the features and elements (and alternatives to such features and elements) of the embodiments illustrated in FIGS. 5-12. Any of the features described above with respect to FIGS. 1-4D can be applied to the embodiments of FIGS. 5-12, and vice versa.

Figure 5:
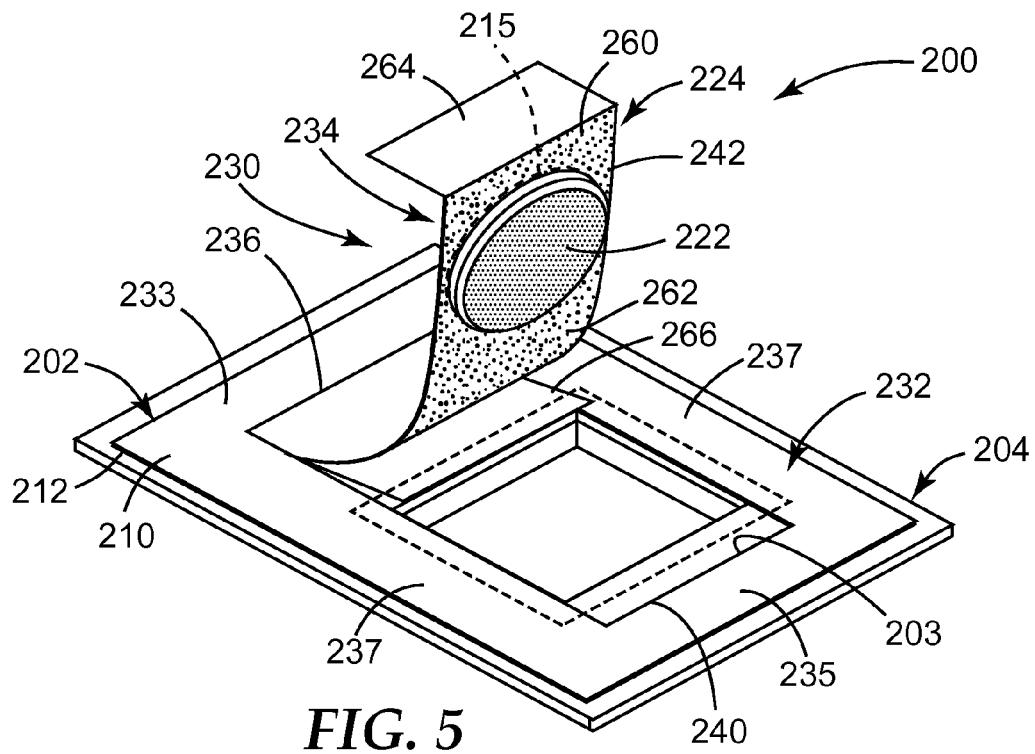
FIG. 5 is a perspective view of a transdermal adhesive patch assembly according to another embodiment of the present disclosure.

FIG. 5 illustrates a transdermal adhesive patch assembly 200 according to another embodiment of the present disclosure. In the transdermal adhesive patch assembly 200, the flap 230 is surrounded on all sides by the anchor 232, such that the patch 202 includes an aperture 203 formed therein. Specifically, in the embodiment shown in FIG. 5, the flap 230 is centrally located with respect to the anchor 232; however, the flap 230 need not be exactly centrally located with respect to the anchor 232. Such a configuration can provide better anchoring of the transdermal adhesive patch assembly 200 to further inhibit the anchor 232 from lifting off from the skin during movement of the flap 230.

When the flap 230 is moved from the first position 240 (shown as being in line with the aperture 203) to the second position 242, the free end 234 of the flap 230 is folded back toward a portion (e.g., a rear portion 233) of the anchor 232. When the flap 230 is moved form the second position 242 to the first position 240, the free end 234 of the flap 230 is folded down toward another portion (e.g., a front portion 235) of the anchor 232. As shown, the anchor 232 can also include one or more side portions 237, depending on where, with the area of the backing 210 (or patch 202), the flap 230 is located.

The flap 230 can also include a portion of the skin-contact adhesive 212 to adhere the matrix 215 to the skin, e.g., in embodiments in which the matrix 215 itself is not adhesive or is weakly adhesive. In such embodiments, the carrier 224 can extend across the entire flap 230 (i.e., under the microneedle array 222), as shown, to cover and protect the skin-contact adhesive 212 during skin treatment, so that the skin-contact adhesive 212 is not worn out or weakened by adhering to the skin during the skin treatment step.

The carrier 224 includes a first extension 260 having a tab 264 and a second extension 262 having a tab 266, similar to the transdermal adhesive patch assembly 100 described above. However, this is shown by way of example only and other carrier embodiments (such as those described below and illustrated in FIGS. 6-11) can be employed.

Figure 6:
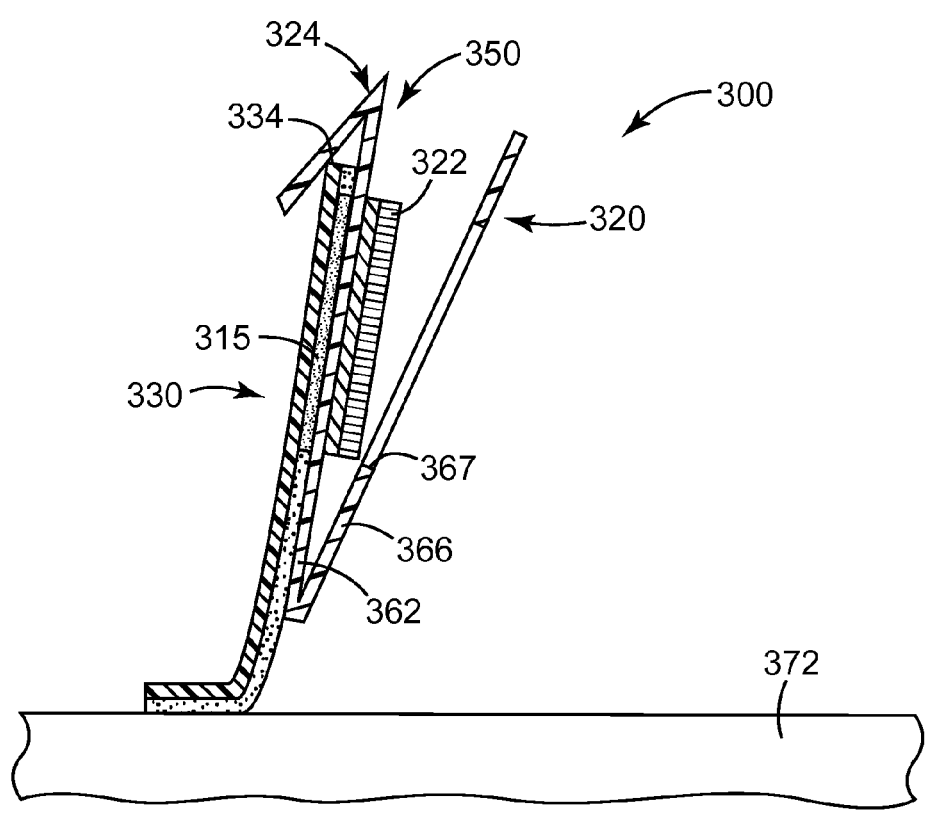
FIG. 6 is a schematic side cross-sectional view of a transdermal adhesive patch assembly according to another embodiment of the present disclosure.

FIG. 6 illustrates a transdermal adhesive patch assembly 300 according to another embodiment of the present disclosure. The transdermal adhesive patch assembly 300 is shown as being adhered to skin 372 while in a skin treatment configuration 350, by way of example only. As shown in FIG. 6, in some embodiments, the tab 366 (if employed) of the second extension 362 (if employed) of the carrier 324 can extend at least partially over the microneedle array 322 toward the free end 334 of the flap 330 to facilitate accessing the tab 366 and removing the skin treatment assembly 320. In some embodiments, as shown in FIG. 6, the tab 366 of the second extension 362 can extend past or over the microneedle array 322, and the tab 366 can include an aperture 367 dimensioned to receive at least a portion of the microneedle array 322 therethrough. Such a configuration can facilitate one-hand use, e.g., one-hand skin treatment, one-hand movement of the flap 330 between the first position (not shown) and the second position 342, one-hand removal of the skin treatment assembly 320, and/or one-hand application of the matrix 115 to a treated area.

Figure 7:
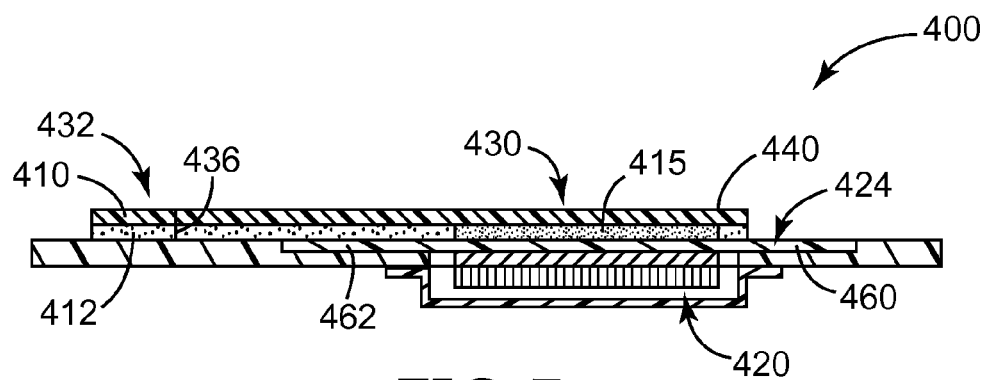
FIG. 7 is a schematic side cross-sectional view of a transdermal adhesive patch assembly according to another embodiment of the present disclosure.
Figure 8:
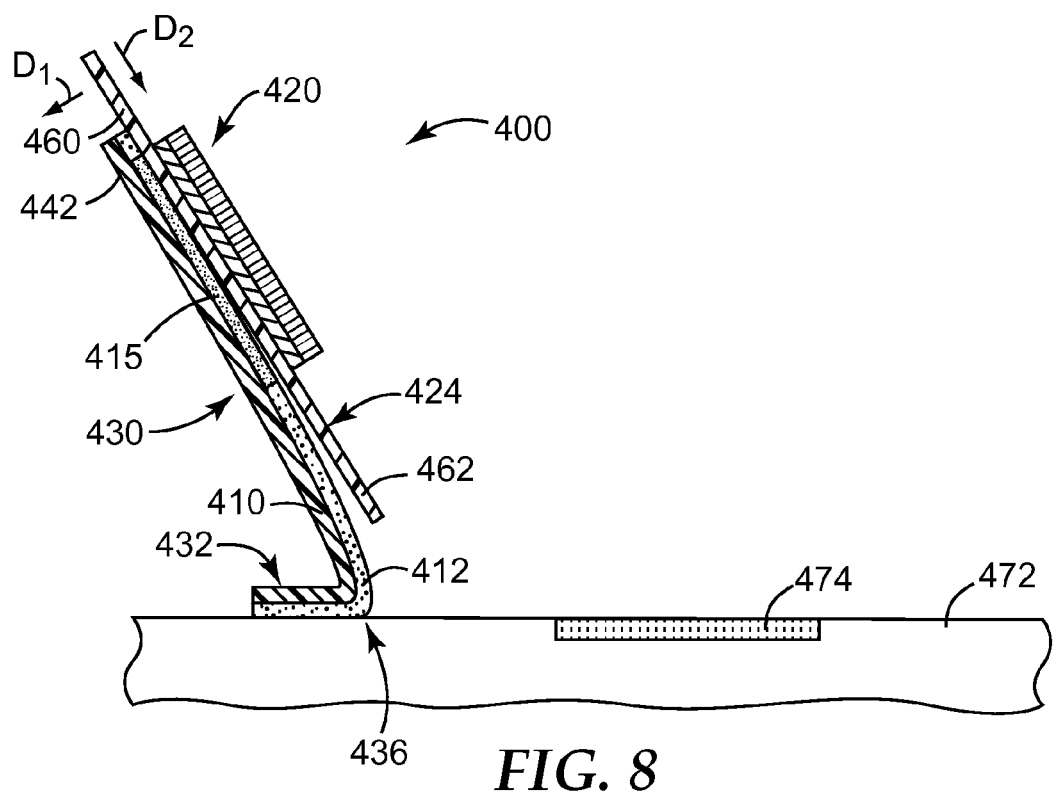
FIG. 8 is a schematic side cross-sectional view of the transdermal adhesive patch assembly of FIG. 7, the transdermal adhesive patch assembly having an anchor that is shown coupled to skin and a flap that is shown peeled back from the skin, in a second position, after an area of the skin has been treated.

FIGS. 7-8 illustrate a transdermal adhesive patch assembly 400 according to another embodiment of the present disclosure. As shown in FIGS. 7-8, in some embodiments, the carrier 424 does not need to include any tabs (or folded portions). Rather, in some embodiments, the first extension 460 and the second extension 462 can be relatively straight and planar. As shown in FIG. 8, in some embodiments, the coefficient of adhesion between the carrier 424 and the skin-contact adhesive 412 and/or the matrix 415 can be weak enough to allow the carrier 424 to be removed by holding onto the first extension 460 and lifting the skin treatment assembly 420 away. Alternatively, as shown in FIG. 8, the carrier 424 (e.g., second extension 462, or the portion near the fixed end 436 of the flap 430) can adhere weakly enough to the adhesive (e.g., the skin-contact adhesive 412 and/or the matrix 415) that as the flap 430 is moved to the second position 442, the carrier 424 (e.g., the second extension 462) can begin to pull away from the adhesive, e.g., near the fixed end 436 of the flap 430.

If the carrier 424 is stiff enough (e.g., relative to the backing 410), the carrier 424 can continue to be removed from the adhesive without grasping the second extension 462, or the second extension 462 can be grasped to remove the skin treatment assembly 420. As shown in FIG. 8, in some embodiments, the carrier 424 can be sufficiently stiff (and/or weakly adhered to the adhesive) such that the skin treatment assembly 420 can be removed from the adhesive by pressing the first extension 460 of the carrier 424 at least partially downward, e.g., in a first direction $D_1$. Alternatively, or additionally, the carrier 424 can be removed by pushing the carrier 424 (i.e., the skin treatment assembly 420) in a direction generally toward the fixed end 436 of the flap 430 and/or toward the second extension 462, shown as second direction $D_2$. The second direction $D_2$ can sometimes be described as in a direction generally opposite the anchor 432. Said another way, the second direction $D_2$ can be described as generally toward the treated area 474 of skin 472. Pressing the carrier 424 in at least one of the first direction $D_1$ and the second direction $D_2$ can allow the skin treatment assembly 420 to be removed using one hand. Motion generally in the direction of $D_2$ can include a shearing action, a peeling action, or a combination thereof.

It should be understood, however, that depending on the size of the carrier, no matter what configuration of carrier is employed in the transdermal adhesive patch assemblies of the present disclosure, the carrier can be removed using one hand. However, some embodiments may be better (or, alternatively, more cumbersome) for one-hand handling than others.

In some embodiments, the carrier 424 does not include any second extension 462. Rather, the (first) extension 460 can be used to move the flap 430 from the first position 440 (see FIG. 7) to the second position 442 (see FIG. 8), and the carrier 424 can be configured such that the extension 460 alone can also be used to remove the skin treatment assembly 420 from the adhesive.

Figure 9:
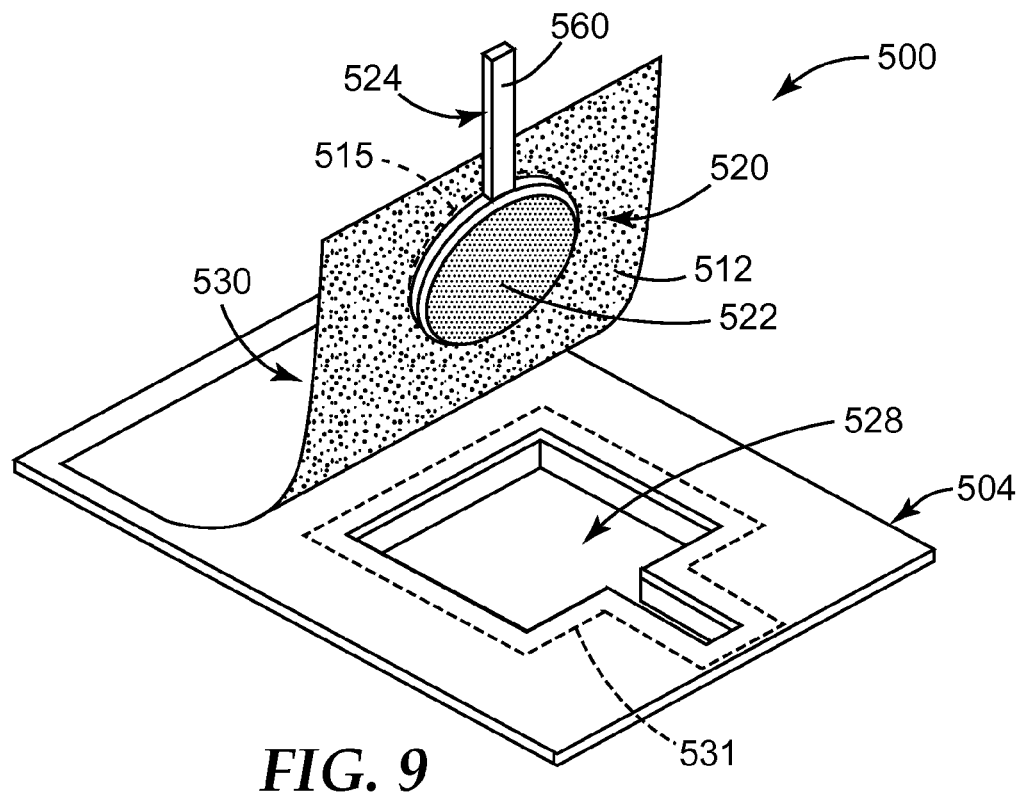
FIG. 9 is a perspective view of a transdermal adhesive patch assembly according to another embodiment of the present disclosure, the transdermal adhesive patch assembly having an anchor and a flap, the flap shown in a second position.
Figure 10:
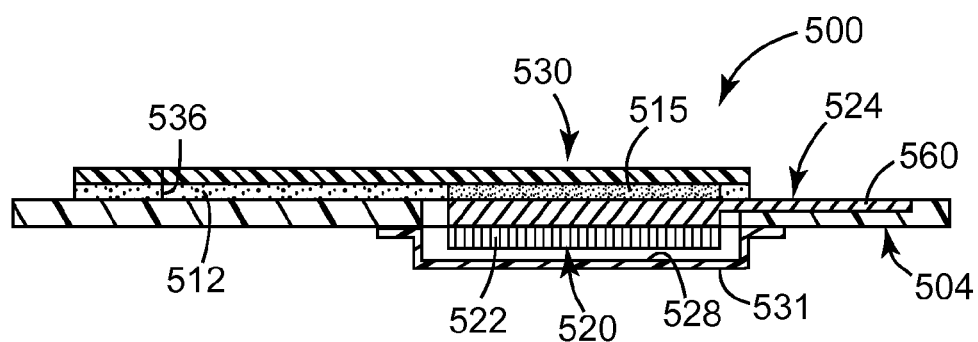
FIG. 10 is a schematic side cross-sectional view of the transdermal adhesive patch assembly of FIG. 9, with the flap shown in a first position.
Figure 11:
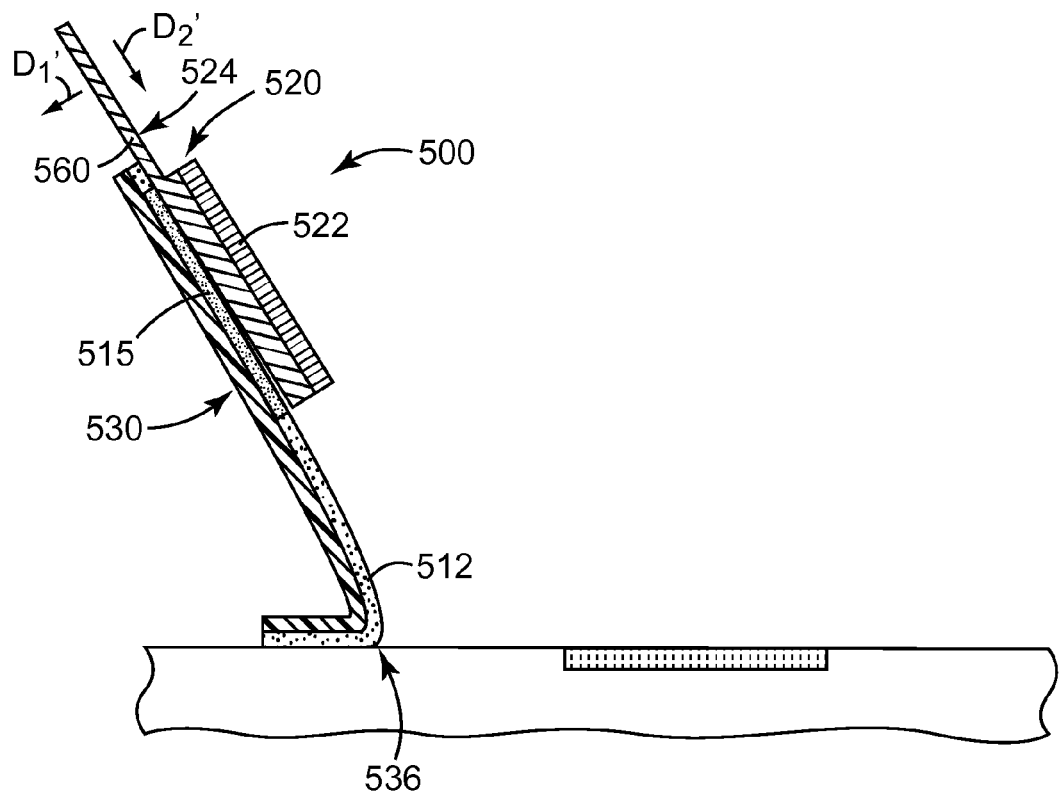
FIG. 11 is a schematic side cross-sectional view of the transdermal adhesive patch assembly of FIGS. 9-10, shown with the anchor coupled to skin and the flap peeled back from the skin, in a second position, after an area of the skin has been treated.

FIGS. 9-11 illustrate a transdermal adhesive patch assembly 500 according to another embodiment of the present disclosure, in which skin treatment assembly 520 includes the carrier 524 and the microneedle array 522 integrally formed together (such that the carrier 524 includes the microneedle array 522, or vice versa). As such, the carrier 524 can essentially just form the (first) extension 560, or the carrier 524 can also at least partially extend under the microneedle array 522, and include the extension 560.

By way of example only, in some embodiments, such a skin treatment assembly 520 can be molded (e.g., injection molded). For example, in some embodiments, a runner from such a molding process can be left extending from the molded microneedle array 522, and the runner can form at least a portion of the carrier 524. Only one runner (i.e., the extension 560) is shown in FIGS. 9-11, but it should be understood that as many desired can be included, for example, a second runner can be employed that can function as a second extension, which can extend generally opposite the extension 560 and which can be used similarly to any of the second extensions 162, 362, 462 described above. Such a molded skin treatment assembly 520 can be formed of a low surface energy material, as described above (e.g., a polyolefin), or can be treated or coated with a release agent in order to present release characteristics to the adhesive (e.g., the skin-contact adhesive 512 and/or the matrix 515).

As shown in FIG. 9, in such embodiments, at least the carrier 524 may be thicker than in other embodiments. As such, the housing 531 included in or coupled to the release liner 504 can be configured to include a recess 528 that is dimensioned to receive the microneedle array 522 and the carrier 524. Alternatively, separates recesses 528 for each of the microneedle array 522 and the carrier 524 can be employed.

By way of example only, the carrier 524 is shown as including only one extension 560; however, it should be understood that additional extensions and/or tabs can be employed. In embodiments employing only one extension 560, the skin treatment assembly 520 can be removed according to any of the methods described above with respect to FIGS. 7-8, for example, by pressing along the first direction $D_1'$ (see FIG. 11) and/or by pushing along the second direction $D_2'$ (see FIG. 11). Such movements can be particularly useful in embodiments in which the skin treatment assembly 520 is formed of polymer (e.g., a rigid, molded polymer). Alternatively, in some embodiments, the end of the microneedle array 522 that is positioned opposite the extension 560 (i.e., toward the fixed end 536 of the flap 530) can be grasped and lifted off of the adhesive.

Figure 12:
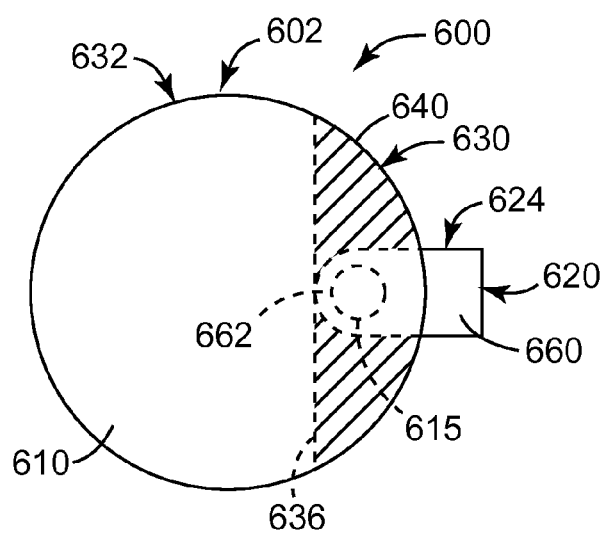
FIG. 12 is a top plan view of a transdermal adhesive patch assembly according to another embodiment of the present disclosure.

FIG. 12 illustrates a top plan view of a transdermal adhesive patch assembly 600 according to another embodiment of the present disclosure, shown with the flap 630 in the first position 640. The transdermal adhesive patch assembly 600 is an example of using a lesser portion of the patch 602 in the flap 630, such that the anchor 632 is large relative to flap 630 and can remain securely adhered to skin when the flap 630 is moved away from the skin. In addition, such a configuration ensures that a lesser portion of skin-contact adhesive (which is located under the backing 610 in FIG. 12) is adhered to the skin during the skin treatment step, so that less of the adhesive needs to be re-applied, which may allow for premature wear of the adhesive. In addition, by way of example only, the carrier 624 includes a first extension 660 that is substantially longer than the second extension 662, which can allow the fixed end 636 of the flap 630 to be positioned closer to an edge of the patch 602.

In some embodiments, at least a portion of the carrier 624 can extend from the fixed end 636 of the flap 630 to an edge of the patch 602 (e.g., as shown in FIG. 12 in cross-hatched lines), such that any adhesive that resides in the flap 630 is covered by the carrier 624. As such, during skin treatment, the adhesive will not prematurely adhere to the skin or experience any wear. Rather, the adhesive will be freshly exposed when the skin treatment assembly 620 is removed, and will be ready to be freshly applied to skin following skin treatment to securely hold the matrix 615 in place over a treated area of skin.

Each embodiment shown in the figures is illustrated as a separate embodiment for clarity in illustrating a variety of features of the transdermal adhesive patch assemblies of the present disclosure. However, it should be understood that any combination of elements and features of any of the embodiments illustrated in the figures and described herein can be employed in the transdermal adhesive patch assemblies of the present disclosure.

The following embodiments are intended to be illustrative of the present disclosure and not limiting.

EMBODIMENTS

Embodiment 1 is a transdermal adhesive patch assembly, the assembly comprising:
a backing having a first major surface and a second major surface;
a skin-contact adhesive coupled to the second major surface of the backing;
a matrix comprising an active ingredient, the matrix coupled to the second major surface of the backing;
a microneedle array located in at least partially overlapping relationship with the matrix; and
a carrier positioned to couple the microneedle array to the matrix opposite the backing, wherein the carrier and the microneedle array form a skin treatment assembly that can be decoupled from the matrix, when desired, to expose the matrix;
wherein a portion of the backing and at least a portion of the skin-contact adhesive extend beyond the skin treatment assembly in at least one direction to form an anchor, and wherein the matrix and the skin treatment assembly are located on a flap that is movable with respect to the anchor between a first position in which the flap is not folded back relative the anchor and a second position in which the flap is folded back relative to the anchor.

Embodiment 2 is a method of treating skin and applying an active ingredient transdermally, the method comprising:
providing a transdermal adhesive patch assembly, the assembly comprising
a backing having a first major surface and a second major surface,
a skin-contact adhesive coupled to the second major surface of the backing,
a matrix comprising an active ingredient, the matrix coupled to the second major surface of the backing,
a microneedle array located in at least partially overlapping relationship with the matrix, and
a carrier positioned to couple the microneedle array to the matrix opposite the backing, the carrier and the microneedle array forming a skin treatment assembly,
adhering at least a portion of the skin-contact adhesive to the skin to form an anchor, wherein the matrix and the skin treatment assembly are located on a flap that is movable with respect to the anchor;
applying pressure adjacent the microneedle array to treat an area of the skin;
moving the flap away from the skin while the anchor remains adhered to the skin;
removing the skin treatment assembly to expose the matrix; and
replacing the flap to position the matrix in least partially overlapping relationship with the treated area of the skin.

Embodiment 3 is the assembly of embodiment 1 or the method of embodiment 2, wherein the flap is movable with respect to the anchor when the anchor is coupled to skin between the first position in which at least one of the matrix and the microneedle array is in contact with skin, and the second position in which neither the matrix nor the microneedle array is in contact with the skin.

Embodiment 4 is the assembly of embodiment 1 or 3 or the method of embodiment 2 or 3, wherein the matrix includes a first major surface coupled to the second major surface of the backing and a second major surface, and wherein the carrier is positioned to couple the microneedle array to the second major surface of the matrix.

Embodiment 5 is the assembly of any of embodiments 1 and 3-4 or the method of any of embodiments 2-4, wherein the carrier includes the microneedle array.

Embodiment 6 is the assembly of any of embodiments 1 and 3-5 or the method of any of embodiments 2-5, wherein the microneedle array and the carrier are adhesively coupled together, and wherein the coefficient of adhesion between the carrier and the matrix is less than the coefficient of adhesion between the matrix and the backing, and is less than the coefficient of adhesion between the carrier and the microneedle array.

Embodiment 7 is the assembly of any of embodiments 1 and 3-6 or the method of any of embodiments 2-6, wherein the carrier is further coupled to the skin-contact adhesive.

Embodiment 8 is the assembly or method of embodiment 7, wherein the coefficient of adhesion between the carrier and the skin-contact adhesive is less than the coefficient of adhesion between the skin-contact adhesive and the backing.

Embodiment 9 is the assembly of any of embodiments 1 and 3-8 or the method of any of embodiments 2-8, wherein the carrier includes release characteristics for at least one of the skin-contact adhesive and the matrix.

Embodiment 10 is the assembly of any of embodiments 1 and 3-9 or the method of any of embodiments 2-9, wherein the carrier includes a release layer for at least one of the skin-contact adhesive and the matrix.

Embodiment 11 is the assembly or method of embodiment 10, wherein the release layer is a first release layer, and further comprising a second release layer that is coupled to the skin-contact adhesive opposite the backing.

Embodiment 12 is the assembly or method of embodiment 11, wherein the second release layer includes a recess dimensioned to receive the microneedle array.

Embodiment 13 is the assembly of any of embodiments 1 and 3-12 or the method of any of embodiments 2-12, wherein the carrier includes an extension that extends beyond an edge of the backing in a direction generally opposite the anchor.

Embodiment 14 is the assembly or method of embodiment 13, wherein the extension includes a tab that is folded back toward the backing.

Embodiment 15 is the assembly or method of embodiment 13 or 14, wherein the extension is a first extension and further comprising a second extension located on an opposite end of the carrier from the first extension, the first extension configured to facilitate moving the flap from the first position to the second position, and the second extension configured to facilitate decoupling the skin treatment assembly from the matrix.

Embodiment 16 is the assembly or method of embodiment 15, wherein the second extension includes a tab that is folded back toward the microneedle array to facilitate grasping.

Embodiment 17 is the assembly or method of embodiment 16, wherein the tab of the second extension extends at least partially over the microneedle array.

Embodiment 18 is the assembly or method of embodiment 16 or 17, wherein the tab of the second extension extends at least partially over the microneedle array and includes an aperture dimensioned to receive the microneedle array to allow the microneedle array to pass therethrough.

Embodiment 19 is the assembly of any of embodiments 1 and 3-18 or the method of any of embodiments 2-18, further comprising a release liner coupled to the skin-contact adhesive opposite the backing and including a recess dimensioned to receive the microneedle array.

Embodiment 20 is the assembly or method of embodiment 19, wherein the recess is further dimensioned to receive at least a portion of the carrier.

Embodiment 21 is the assembly of any of embodiments 1 and 3-20 or the method of any of embodiments 2-20, wherein the assembly includes:
  a skin treatment configuration wherein the skin treatment assembly is coupled to the matrix, such that the matrix is at least partially covered by the skin treatment assembly, and
  a delivery configuration wherein the skin treatment assembly has been removed/decoupled from the matrix to expose the matrix for delivery of the active ingredient.

Embodiment 22 is the assembly of any of embodiments 1 and 3-21 or the method of any of embodiments 2-21, wherein the anchor surrounds the flap on all sides.

Embodiment 23 is the assembly of any of embodiments 1 and 3-22 or the method of any of embodiments 2-22, wherein a portion of the skin-contact adhesive extends alongside the skin treatment assembly in the flap, such that when the microneedle array is positioned in contact with skin, at least a portion of the skin-contact adhesive in the flap is adhered to the skin.

Embodiment 24 is the assembly of any of embodiments 1 and 3-22 or the method of any of embodiments 2-22, wherein a portion of the skin-contact adhesive extends alongside the matrix and the microneedle array in the flap, and wherein the carrier is positioned to cover the portion of the skin-contact adhesive that is located in the flap, such that when the microneedle array is positioned in contact with the skin, the skin-contact adhesive in the flap is not adhered to the skin.

Embodiment 25 is the method of any of embodiments 2-24, wherein the matrix covers the entire treated area of the skin when the flap is replaced.

Embodiment 26 is the method of any of embodiments 2-25, wherein the flap is movable with respect to the anchor between a first position in which the flap is not folded back relative to the anchor and a second position in which the flap is folded back relative to the anchor, wherein applying pressure adjacent the microneedle array occurs while the flap is in the first position, wherein moving the flap away from the skin includes moving the flap from the first position to the second position, and wherein replacing the flap includes moving the flap from the second position to the first position.

Embodiment 27 is the method of any of embodiments 2-26, wherein:
  applying pressure adjacent the microneedle array occurs while the assembly is in a skin treatment configuration in which the matrix is at least partially covered by the skin treatment assembly;
  removing the skin treatment assembly to expose the matrix changes the assembly from the skin treatment configuration to a delivery configuration; and
  replacing the flap occurs while the assembly is in the delivery configuration.

Embodiment 28 is the method of any of embodiments 2-27, wherein the carrier includes an extension that extends beyond an edge of the backing in a direction generally opposite the anchor, and wherein moving the flap away from the skin includes grasping the extension of the carrier.

Embodiment 29 is the method of any of embodiments 2-28, wherein the carrier includes an extension that extends beyond an edge of the backing in a direction generally opposite the anchor, wherein the extension includes a tab that is folded back toward the backing, and wherein moving the flap away from the skin includes grasping the tab.

Embodiment 30 is the method of embodiment 28 or 29, wherein removing the skin treatment assembly includes grasping the extension.

Embodiment 31 is the method of any of embodiments 28-30, wherein removing the skin treatment assembly includes grasping the extension and pushing the skin treatment assembly in a direction toward the treated area of the skin.

Embodiment 32 is the method of any of embodiments 28-31, wherein the extension is a first extension and further comprising a second extension located on an opposite end of the carrier from the first extension, wherein removing the skin treatment assembly includes grasping the second extension.

Embodiment 33 is the method of any of embodiments 28-32, wherein the extension is a first extension and further comprising a second extension located on an opposite end of the carrier from the first extension, wherein the second extension includes a tab that is folded back toward the microneedle array, and wherein removing the skin treatment assembly includes grasping the tab of the second extension.

Embodiment 34 is the method of embodiment 33, wherein the tab of the second extension extends at least partially over the microneedle array.

Embodiment 35 is the method of embodiment 33 or 34, wherein the tab of the second extension extends at least partially over the microneedle array and includes an aperture dimensioned to receive the microneedle array to allow the microneedle array to pass therethrough.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A transdermal adhesive patch assembly, the assembly comprising:
    a backing having a first major surface and a second major surface;
    a skin-contact adhesive coupled to the second major surface of the backing;
    a matrix comprising an active ingredient, the matrix coupled to the second major surface of the backing;
    a microneedle array located in at least partially overlapping relationship with the matrix; and
    a carrier positioned to couple the microneedle array to the matrix opposite the backing, wherein the carrier and the microneedle array form a skin treatment assembly that is configured to be decoupled from the matrix, when desired, to expose the matrix;
    wherein a portion of the backing and at least a portion of the skin-contact adhesive extend beyond the skin treatment assembly in at least one direction to form an anchor, and wherein the matrix and the skin treatment assembly are located on a flap that is movable with respect to the anchor between a first position in which the flap is not folded back relative to the anchor and a second position in which the flap is folded back relative to the anchor.

2. The assembly of claim 1, wherein the flap is movable with respect to the anchor when the anchor is coupled to skin between the first position in which at least one of the matrix and the microneedle array is in contact with skin, and the second position in which neither the matrix nor the microneedle array is in contact with the skin.

3. The assembly of claim 1, wherein the matrix includes a first major surface coupled to the second major surface of the backing and a second major surface, and wherein the carrier is positioned to couple the microneedle array to the second major surface of the matrix.

4. The assembly of claim 1, wherein the carrier includes the microneedle array.

5. The assembly of claim 1, wherein the microneedle array and the carrier are adhesively coupled together, and wherein a coefficient of adhesion between the carrier and the matrix is less than a coefficient of adhesion between the matrix and the backing, and is less than a coefficient of adhesion between the carrier and the microneedle array.

6. The assembly of claim 1, wherein the carrier is further coupled to the skin-contact adhesive.

7. The assembly of claim 6, wherein a coefficient of adhesion between the carrier and the skin-contact adhesive is less than a coefficient of adhesion between the skin-contact adhesive and the backing.

8. The assembly of claim 1, wherein the carrier includes release characteristics for at least one of the skin-contact adhesive and the matrix.

9. The assembly of claim 1, wherein the carrier includes an extension that extends beyond an edge of the backing in a direction generally opposite the anchor.

10. The assembly of claim 9, wherein the extension includes a tab that is folded back toward the backing.

11. The assembly of claim 9, wherein the extension is a first extension and further comprising a second extension located on an opposite end of the carrier from the first extension, the first extension configured to facilitate moving the flap from the first position to the second position, and the second extension configured to facilitate decoupling the skin treatment assembly from the matrix.

12. The assembly of claim 11, wherein the second extension includes a tab that is folded back toward the microneedle array to facilitate grasping.

13. The assembly of claim 12, wherein the tab of the second extension extends at least partially over the microneedle array.

14. The assembly of claim 12, wherein the tab of the second extension extends at least partially over the microneedle array and includes an aperture dimensioned to receive the microneedle array to allow the microneedle array to pass therethrough.

15. The assembly of claim 1, further comprising a release liner coupled to the skin-contact adhesive opposite the backing and including a recess dimensioned to receive the microneedle array.

16. The assembly of claim 1, wherein the assembly includes:
    a skin treatment configuration wherein the skin treatment assembly is coupled to the matrix, such that the matrix is at least partially covered by the skin treatment assembly, and
    a delivery configuration wherein the skin treatment assembly has been decoupled from the matrix to expose the matrix for delivery of the active ingredient.

17. The assembly of claim 1, wherein the anchor surrounds the flap on all sides.

18. The assembly of claim 1, wherein a portion of the skin-contact adhesive extends alongside the skin treatment assembly in the flap, such that when the microneedle array is positioned in contact with skin, at least a portion of the skin-contact adhesive in the flap is adhered to the skin.

19. The assembly of claim 1, wherein a portion of the skin-contact adhesive extends alongside the matrix and the microneedle array in the flap, and wherein the carrier is positioned to cover the portion of the skin-contact adhesive that is located in the flap, such that when the microneedle array is positioned in contact with the skin, the skin-contact adhesive in the flap is not adhered to the skin.

20. A method of treating skin and applying an active ingredient transdermally, the method comprising:
providing a transdermal adhesive patch assembly, the assembly comprising
a backing having a first major surface and a second major surface,
a skin-contact adhesive coupled to the second major surface of the backing,
a matrix comprising an active ingredient, the matrix coupled to the second major surface of the backing,
a microneedle array located in at least partially overlapping relationship with the matrix, and
a carrier positioned to couple the microneedle array to the matrix opposite the backing, the carrier and the microneedle array forming a skin treatment assembly,
adhering at least a portion of the skin-contact adhesive to the skin to form an anchor, wherein the matrix and the skin treatment assembly are located on a flap that is movable with respect to the anchor;
applying pressure adjacent the microneedle array to treat an area of the skin;
moving the flap away from the skin while the anchor remains adhered to the skin;
removing the skin treatment assembly to expose the matrix; and
replacing the flap to position the matrix in least partially overlapping relationship with the treated area of the skin.

* * * * *

UNITED STATES PATENT AND TRADEMARK OFFICE
CERTIFICATE OF CORRECTION

PATENT NO. : 9,144,671 B2
APPLICATION NO. : 14/352327
DATED : September 29, 2015
INVENTOR(S) : Adam Cantor Page 1 of 1

It is certified that error appears in the above-identified patent and that said Letters Patent is hereby corrected as shown below:

In The Specification

Column 4
Line 11, Delete "do no" and insert -- do not --, therefor.

Column 13
Line 33, Delete "antiprotazoals" and insert -- antiprotozoals --, therefor.
Line 49-50, Delete "prilocalne);" and insert -- prilocaine); --, therefor.
Line 57, Delete "exanatide);" and insert -- exenatide); --, therefor.
Line 63, Delete "sumatripan," and insert -- sumatriptan, --, therefor.
Line 64, Delete "flecamide);" and insert -- flecainide); --, therefor.
Line 65, Delete "metaclopromide," and insert -- metoclopramide, --, therefor.

Column 14
Line 37, Delete "pamedronate;" and insert -- pamidronate; --, therefor.

Column 17
Line 21, Delete "form" and insert -- from --, therefor.

Signed and Sealed this
Fifteenth Day of March, 2016

Michelle K. Lee
*Director of the United States Patent and Trademark Office*